US010422742B2

(12) United States Patent
Safai et al.

(10) Patent No.: US 10,422,742 B2
(45) Date of Patent: Sep. 24, 2019

(54) MOISTURE DETECTION SYSTEM

(71) Applicant: The Boeing Company, Chicago, IL (US)

(72) Inventors: Morteza Safai, Newcastle, WA (US); Xiaoxi Wang, Mukilteo, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/787,201

(22) Filed: Oct. 18, 2017

(65) Prior Publication Data

US 2019/0113450 A1 Apr. 18, 2019

(51) Int. Cl.
*G01N 21/3554* (2014.01)
*G01N 25/72* (2006.01)
*G01N 22/04* (2006.01)

(52) U.S. Cl.
CPC ......... *G01N 21/3554* (2013.01); *G01N 22/04* (2013.01); *G01N 25/72* (2013.01); *G01N 2201/0696* (2013.01)

(58) Field of Classification Search
CPC ................. G01N 21/3554; G01N 2021/0696
USPC ................. 250/338.1, 339.1, 339.01, 339.06
See application file for complete search history.

(56) References Cited

U.S. PATENT DOCUMENTS

| | | | | | |
|---|---|---|---|---|---|
| 3,216,241 | A | * | 11/1965 | Hansen | G01N 25/56 374/31 |
| 4,015,366 | A | * | 4/1977 | Hall, III | A01D 46/005 137/236.1 |
| 4,193,027 | A | | 3/1980 | Wyslouzil | |
| 4,236,109 | A | * | 11/1980 | Ingle, Jr. | G01N 27/225 324/687 |
| 4,319,185 | A | * | 3/1982 | Hill | G01R 27/04 324/631 |
| 4,345,150 | A | * | 8/1982 | Tamura | G01N 21/86 250/339.1 |

(Continued)

FOREIGN PATENT DOCUMENTS

| | | |
|---|---|---|
| CN | 201449376 U | 5/2010 |
| CN | 203011859 U | 6/2013 |

(Continued)

OTHER PUBLICATIONS

"Moron et al.,""Measurement of Moisture in Wood for Application in the Restoration of Old Buildings,""Sensors 2016, vol. 16, Issue 5, 9 pages".

(Continued)

*Primary Examiner* — David P Porta
*Assistant Examiner* — Blake C Riddick
(74) *Attorney, Agent, or Firm* — Yee & Associates, P.C.

(57) ABSTRACT

A method and system for an aerospace vehicle. A pulse of electromagnetic radiation is transmitted into the composite sandwich panel such that the composite sandwich panel is heated above an ambient temperature. An amount of infrared radiation generated in the composite sandwich panel is detected in response to transmitting the pulse of electromagnetic radiation into the composite sandwich panel using a time window selected to detect the amount of infrared radiation when the pulse of electromagnetic radiation heats the composite sandwich panel. The amount of infrared radiation detected indicates a level of moisture in the composite sandwich panel.

31 Claims, 11 Drawing Sheets

(56) References Cited

U.S. PATENT DOCUMENTS

| | | | | |
|---|---|---|---|---|
| 4,475,080 A | * | 10/1984 | Walker | G01N 22/04 324/608 |
| 4,532,797 A | * | 8/1985 | Yang | G01N 27/18 324/696 |
| 4,612,802 A | * | 9/1986 | Clarke | G01N 33/46 374/45 |
| 4,674,325 A | | 6/1987 | Kiyobe et al. | |
| 4,733,078 A | * | 3/1988 | Sturm | G01N 33/346 250/339.1 |
| 4,798,956 A | * | 1/1989 | Hochstein | B60S 1/0822 15/DIG. 15 |
| 4,840,706 A | * | 6/1989 | Campbell | G01N 21/3554 162/198 |
| 4,845,978 A | * | 7/1989 | Whitford | G01N 25/18 73/73 |
| 4,871,917 A | * | 10/1989 | O'Farrell | B60S 1/0822 250/341.7 |
| 4,928,013 A | * | 5/1990 | Howarth | D21F 7/003 250/339.1 |
| 4,965,451 A | * | 10/1990 | Solter | G01N 21/171 250/330 |
| 5,124,552 A | * | 6/1992 | Anderson | D21F 7/003 250/339.04 |
| 5,220,168 A | * | 6/1993 | Adamski | G01N 21/3554 250/339.1 |
| 5,315,258 A | * | 5/1994 | Jakkula | G01N 22/04 324/634 |
| 5,433,106 A | * | 7/1995 | Matsumura | G01N 25/56 374/124 |
| 5,870,926 A | * | 2/1999 | Saito | G01N 21/3151 250/339.1 |
| 6,111,415 A | * | 8/2000 | Moshe | G01N 22/04 324/640 |
| 6,124,594 A | * | 9/2000 | Duggan | G01N 21/3563 250/339.06 |
| 6,343,534 B1 | | 2/2002 | Khanna et al. | |
| 6,410,916 B1 | * | 6/2002 | Jost | G01J 5/06 250/332 |
| 7,494,567 B2 | | 2/2009 | Haran | |
| 7,612,799 B1 | * | 11/2009 | Frank | H04N 5/33 250/330 |
| 8,248,256 B1 | * | 8/2012 | Gerardi | G08B 21/20 340/604 |
| 8,779,362 B1 | * | 7/2014 | Amundsen | G01N 21/35 250/339.01 |
| 2002/0018510 A1 | | 2/2002 | Murphy et al. | |
| 2006/0043269 A1 | * | 3/2006 | Zimmerman | G01N 21/3554 250/227.25 |
| 2006/0114965 A1 | | 6/2006 | Murphy et al. | |
| 2006/0243931 A1 | * | 11/2006 | Haran | G01N 21/3554 250/574 |
| 2007/0137823 A1 | * | 6/2007 | Haran | D21F 7/003 162/198 |
| 2008/0079625 A1 | | 4/2008 | Weems et al. | |
| 2008/0107147 A1 | * | 5/2008 | Kollgaard | G01N 25/72 374/5 |
| 2009/0040099 A1 | | 2/2009 | Young et al. | |
| 2010/0051905 A1 | * | 3/2010 | Iguchi | B82Y 20/00 257/14 |
| 2010/0066386 A1 | * | 3/2010 | Dos Santos | G01N 22/04 324/640 |
| 2010/0155603 A1 | * | 6/2010 | Ferreira Dos Santos | G01N 22/04 250/341.6 |
| 2011/0264258 A1 | * | 10/2011 | Ding | G01N 21/3554 700/214 |
| 2012/0330569 A1 | | 12/2012 | Singh et al. | |
| 2014/0000381 A1 | * | 1/2014 | Zuardy | B64C 3/20 73/802 |
| 2014/0246590 A1 | * | 9/2014 | Ishii | G01N 21/21 250/339.1 |
| 2014/0276504 A1 | * | 9/2014 | Heil | A61F 13/42 604/361 |
| 2014/0374598 A1 | * | 12/2014 | Hegeman | G01N 33/0098 250/339.03 |
| 2016/0178510 A1 | * | 6/2016 | Meulendijks-Kiggen | C09D 5/00 250/339.01 |
| 2017/0108433 A1 | * | 4/2017 | Helfmann | G01J 3/0291 |
| 2017/0115210 A1 | * | 4/2017 | Fujiyama | G01N 21/3554 |
| 2018/0059014 A1 | * | 3/2018 | Ruback | H04N 5/23293 |
| 2018/0180538 A1 | * | 6/2018 | Malchow | G01N 21/3554 |
| 2018/0251235 A1 | * | 9/2018 | Bolton | B64F 1/364 |

FOREIGN PATENT DOCUMENTS

| | | |
|---|---|---|
| CN | 203949881 U | 11/2014 |
| CN | 104297265 A | 1/2015 |
| EP | 1455180 A1 | 9/2004 |
| JP | 2014002073 A | 1/2014 |
| WO | WO0244700 A1 | 6/2002 |

OTHER PUBLICATIONS

Safai et al., "Synchronized Phased Array and Infrared Detector System for Moisture Detection," U.S. Appl. No. 15/787,014, filed Oct. 18, 2017, 65 pages.

European Patent Office Partial Search Report, dated Feb. 5, 2019, regarding Application No. 18186967.8, 11 pages.

Intellectual Property Office of The United Kingdom Combined Search and Examination Report, dated Apr. 8, 2019, regarding Application No. GB1816497.0, 9 pages.

Office Action, dated Mar. 27, 2019 regarding U.S. Appl. No. 15/787,014, 37 pages.

* cited by examiner

| RF WAVE PENETRATION: | | | | |
|---|---|---|---|---|
| | ELECTRICAL CONDUCTIVITY (%IACS) | MAGNETIC PERMEABILITY (H/mm) | FREQUENCY (Hz) | DEPTH OF PENETRATION (mm) |
| EXAMPLE MATERIAL | 10% | $1 \times 10^{-9}$ | $1 \times 10^{9}$ | 1.78 |

MOISTURE DETECTION SYSTEM

CROSS-REFERENCE TO RELATED APPLICATION

This application is related to the following U.S. patent application Ser. No. 15/787,014, entitled "Synchronized Phased Array and Infrared Detector System for Moisture Detection," filed even date herewith, and incorporated herein by reference in its entirety.

BACKGROUND INFORMATION

1. Field

The present disclosure relates generally to aircraft and, in particular, to detecting moisture in porous materials in aircraft. Still more particularly, the present disclosure relates to a method, apparatus, and system for detecting moisture in panels in aircraft.

2. Background

Aircraft are being designed and manufactured with greater and greater percentages of composite materials. Composite materials are used in aircraft to decrease the weight of the aircraft. This decreased weight improves performance features such as payload capacities and fuel efficiencies. Further, composite materials provide a longer service life for various components in an aircraft.

For example, composite parts such as composite panels are used in aircraft for walls, closets, galleys, and other structures or monuments in aircraft such as commercial airplanes. These composite panels may be composite sandwich panels that are comprised of a core between two face sheets. The core may be a honeycomb core, a foam core, or some other suitable type of core. Further, in some cases, a decorative laminate may be placed on a face sheet or may be used as the face sheet. In this manner, the composite sandwich panel may have logos, color, or designs for a particular airline.

One problem with these composite sandwich panels and other structures that have porous materials is moisture. Moisture in a composite sandwich panel can cause bubbling. Bubbling is aesthetically undesirable especially when the bubbling occurs in locations visible to passengers, such as in the passenger cabin within a commercial airplane.

This occurrence in a structure in the passenger cabin is a problem that can disrupt the delivery of a commercial airplanes when bubbling is discovered. Further, the discovery of bubbling in composite sandwich panels during production of a commercial airplane may result in delays. Reworking composite sandwich panels with bubbling increases the time and expense for producing an airplane. Disruption in the production line may occur.

Further, moisture within a composite sandwich panel may not immediately manifest itself in the form of bubbling. When bubbling is discovered, rework may be performed.

Therefore, it would be desirable to have a method and apparatus that take into account at least some of the issues discussed above, as well as other possible issues. For example, it would be desirable to have a method and apparatus that overcome a limitation with detecting moisture in porous structures such as composite sandwich panels.

SUMMARY

An example of the present disclosure provides a moisture detection system. The moisture detection system is comprised of an electromagnetic radiation system, an infrared detector system, and a controller in communication with the electromagnetic radiation system and the infrared detector system. The controller is configured to control the electromagnetic radiation system to transmit a pulse of electromagnetic radiation into a composite sandwich pane. The pulse of electromagnetic radiation has a number of wavelengths that is absorbed by water molecules. The controller is configured to control the infrared detector system to detect an amount of infrared radiation in response to transmitting the pulse of electromagnetic radiation into the composite sandwich panel using a time window. The time window is selected to detect the amount of infrared radiation when the pulse of electromagnetic radiation heats the composite sandwich panel such that the infrared detector system detects the amount of infrared radiation in the composite sandwich panel when the composite sandwich panel is heated by the pulse of electromagnetic radiation. The amount of infrared radiation indicates a level of moisture in the composite sandwich panel.

Another embodiment of the present disclosure provides a method for an aerospace vehicle. A pulse of electromagnetic radiation is transmitted into the composite sandwich panel such that the composite sandwich panel is heated above an ambient temperature. An amount of infrared radiation generated in the composite sandwich panel is detected in response to transmitting the pulse of electromagnetic radiation into the composite sandwich panel using a time window selected to detect the amount of infrared radiation when the pulse of electromagnetic radiation heats the composite sandwich panel. The amount of infrared radiation detected indicates a level of moisture in the composite sandwich panel.

Yet another embodiment of the present disclosure provides a moisture detection system. The moisture detection system is comprised of an electromagnetic radiation system an infrared detector system, and a controller. The controller is configured to control the electromagnetic radiation system to transmit a pulse of electromagnetic radiation into a porous material in which a pulse of electromagnetic radiation beam has a number of wavelengths that is absorbed by water molecules. The controller is configured to control the infrared detector system to detect the amount of infrared radiation in the porous material in response to transmitting the pulse of electromagnetic radiation into the porous material using a time window that captures when the pulse of electromagnetic radiation heats the porous material such that the infrared detector system detects the amount of infrared radiation in the porous material when the porous material is heated by the pulse of electromagnetic radiation. The controller is configured to identify a level of moisture in the porous material using an amount of energy in the pulse of electromagnetic radiation transmitted and the amount of infrared radiation detected.

Another embodiment of the present disclosure provides a method for detecting moisture in a porous material. Electromagnetic radiation is transmitted into the porous material, wherein an electromagnetic radiation beam has a number of wavelengths that is absorbed by water molecules. An amount of infrared radiation in the porous material is detected in response to transmitting the electromagnetic radiation into a composite sandwich panel using a time window selected to detect the amount of infrared radiation when the electromagnetic radiation heats the porous material. A level of moisture in the porous material is identified using an amount of energy in the electromagnetic radiation transmitted and the amount of infrared radiation detected.

The features and functions can be achieved independently in various examples of the present disclosure or may be combined in yet other examples in which further details can be seen with reference to the following description and drawings.

BRIEF DESCRIPTION OF THE DRAWINGS

The novel features believed characteristic of the illustrative examples are set forth in the appended claims. The illustrative examples, however, as well as a preferred mode of use, further objectives and features thereof, will best be understood by reference to the following detailed description of an illustrative example of the present disclosure when read in conjunction with the accompanying drawings, wherein:

DETAILED DESCRIPTION

Figure 1:
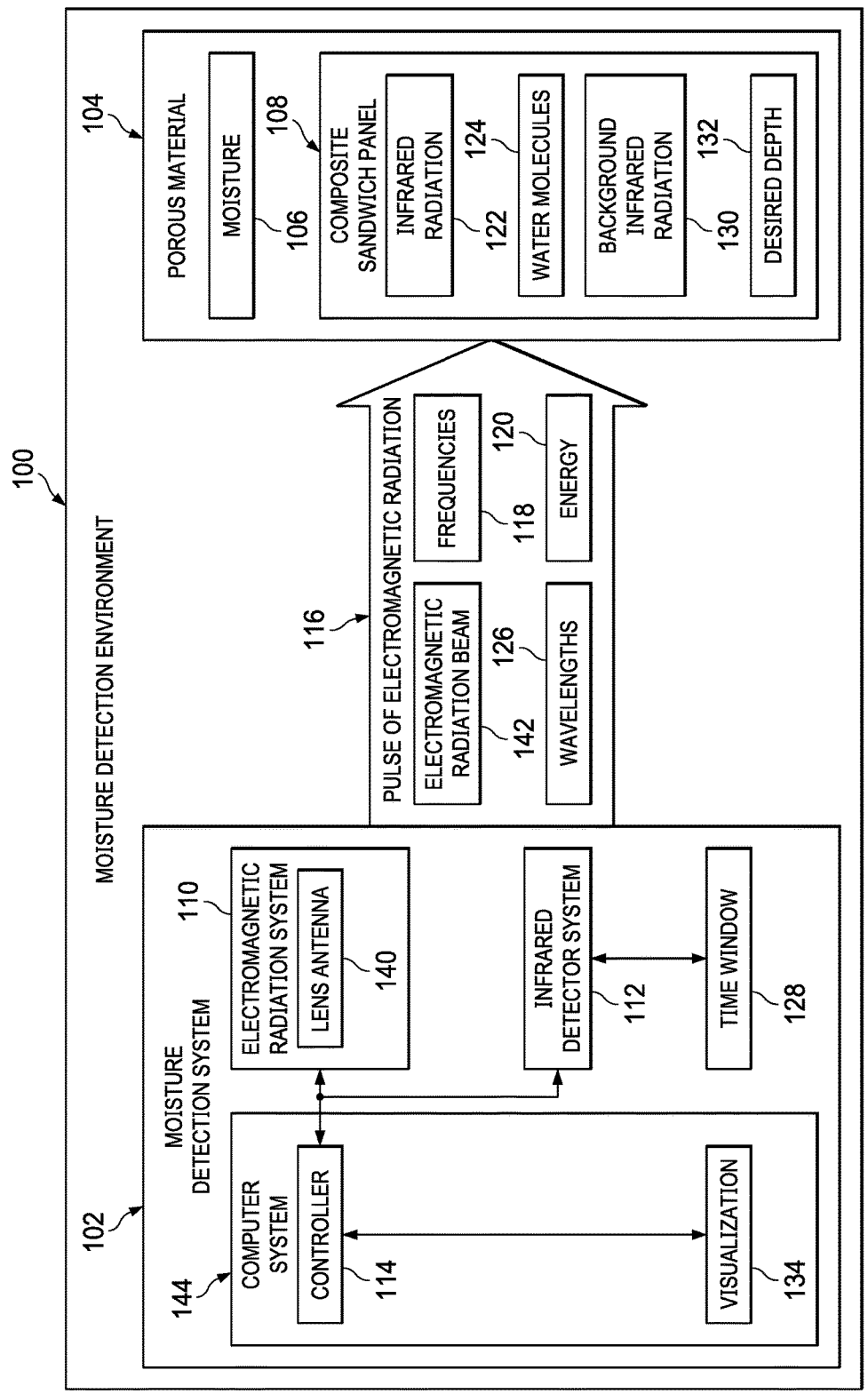
FIG. 1 is an illustration of a block diagram of a moisture detection environment in accordance with an illustrative example.

The illustrative examples recognize and take into account one or more different considerations. For example, the illustrative examples recognize and take into account that measuring moisture in composite sandwich structures that employ foam or honeycomb cores may be more difficult than desired. The illustrative examples recognize and take into account that current techniques for moisture detection are unable to measure a level of moisture in a composite sandwich structure. The illustrative examples recognize and take into account that current techniques are unable to map the level of moisture in a composite sandwich structure.

Thus, the illustrative examples provide a method, apparatus, and system for detecting moisture. In one illustrative example, a moisture detection system comprises an electromagnetic radiation system, an infrared detector system, and a controller. The electromagnetic radiation system is configured to transmit electromagnetic radiation, and the infrared detector system is configured to detect an amount of infrared energy.

The controller is configured to control the electromagnetic radiation system to transmit a pulse of electromagnetic radiation into the porous material, in which the pulse of the electromagnetic radiation beam has a number of wavelengths that is absorbed by water molecules. The controller also controls the infrared detector system to detect the amount of infrared energy in the porous material in response to transmitting the electromagnetic radiation into the porous material using a time window that captures when the electromagnetic radiation heats the porous material such that the infrared detector system detects an amount of the infrared energy in the porous material when the porous material is heated by the pulse of electromagnetic radiation. The controller identifies a level of moisture in the porous material using an amount of energy in the electromagnetic radiation transmitted and the amount of infrared energy detected.

In another illustrative example, a moisture detection system comprises a phased array, an infrared detector system, and a controller. The phased array is configured to emit a pulse of an electromagnetic radiation beam. The pulse of the electromagnetic radiation beam has a number of wavelengths that is absorbed by water molecules. The infrared detector system is configured to detect an amount of infrared energy. The amount of infrared energy indicates a level of moisture in a porous material.

The controller is configured to control the phased array by beam steering the pulse of the electromagnetic radiation beam to an area on the porous material, and synchronize timing of the pulse of the electromagnetic radiation beam to heat the porous material with a time window in the infrared detector system to detect the amount of infrared energy. The controller is configured to control the infrared detector system to detect the amount of the infrared energy in an area on the porous material in the time window when the porous material is heated by the pulse of the electromagnetic radiation beam.

With reference now to the figures, and in particular, with reference to FIG. 1, an illustration of a block diagram of a moisture detection environment is depicted in accordance with an illustrative example. In this illustrative example, moisture detection environment 100 includes moisture detection system 102, which operates to inspect porous material 104. In this example, porous material 104 can be inspected for a level of moisture 106. As depicted, the level of moisture 106 may indicate a presence or absence of moisture 106. When moisture 106 is present, the level of moisture 106 can also indicate how much moisture 106 is detected.

In this illustrative example, porous material 104 is a material having spaces, holes, or other types of channels or voids through which a liquid or gas can pass. For example, porous material 104 can be an open cell foam or honeycomb structure. In another example, porous material 104 may be a closed cell foam in which some cells are not closed and allows a gas or liquid to pass.

In the illustrative example, porous material 104 takes the form of composite sandwich panel 108. Composite sandwich panel 108 comprises a core located between a first face sheet and a second face sheet. The core may take a number of different forms. For example, the core can be selected from at least one of a foam core, an open cell foam core, a closed cell foam core, a honeycomb core, or some other suitable type of core.

As used herein, the phrase "at least one of," when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category.

For example, without limitation, "at least one of item A, item B, or item C" may include item A, item A and item B, or item B. This example also may include item A, item B, and item C or item B and item C. Of course, any combinations of these items may be present. In some illustrative examples, "at least one of" may be, for example, without limitation, two of item A; one of item B; and ten of item C; four of item B and seven of item C; or other suitable combinations.

As depicted, the type of core within composite sandwich panel 108 can be different in different parts of composite sandwich panel 108. For example, a portion of composite sandwich panel 108 may be a honeycomb core in one area of composite sandwich panel 108 and a foam core in another area of composite sandwich panel 108. In one illustrative example, composite sandwich panel 108 is for use in an aerospace vehicle selected from one of an airplane, an aircraft, a commercial airplane, a rotorcraft, a spacecraft, a commercial spacecraft, a space plane, or some other type of aerospace vehicle.

In this illustrative example, moisture detection system 102 is comprised of a number of different components. As depicted, moisture detection system 102 includes electromagnetic radiation system 110, infrared detector system 112, and controller 114.

Electromagnetic radiation system 110 transmits pulse of electromagnetic radiation 116. In this illustrative example, pulse of electromagnetic radiation 116 has a number of frequencies 118 selected from about 300 MHz to about 300 GHz.

As used herein, "a number of," when used in reference to items means one or more items. For example, "a number of frequencies 118" is one or more of frequencies 118. In this example, pulse of electromagnetic radiation 116 takes the form of pulse of microwaves. Pulse of electromagnetic radiation 116 is the transmission of electromagnetic radiation for a period of time in contrast to transmitting electromagnetic radiation continuously while operating moisture detection system 102.

In this illustrative example, infrared detector system 112 is configured to detect an amount of infrared radiation 122. As depicted, infrared radiation 122 has a longer wavelength than those of visible light. In this illustrative example, infrared radiation 122 is generated when pulse of electromagnetic radiation 116 encounters water molecules 124 in moisture 106.

Infrared detector system 112 includes a number of different types of detectors. For example, infrared detector system 112 may include at least one of an infrared sensor, a thermal sensor, a photodetector, a thermographic camera, an infrared camera, a thermal imaging camera, or some other suitable type of detector.

In this illustrative example, controller 114 is in communication with electromagnetic radiation system 110 and infrared detector system 112. Controller 114 is configured to control electromagnetic radiation system 110 to transmit pulse of electromagnetic radiation 116 into composite sandwich panel 108. Pulse of electromagnetic radiation 116 has a number of wavelengths 126 such that pulse of electromagnetic radiation 116 is absorbed water molecules 124 in moisture 106 in composite sandwich panel 108.

As depicted, controller 114 is configured to select the number of frequencies 118 for pulse of electromagnetic radiation 116 based on desired depth 132 at which pulse of electromagnetic radiation 116 penetrates composite sandwich panel 108. The level of penetration affects the depth at which heating within composite sandwich panel 108 occurs.

Further, controller 114 can be configured to control electromagnetic radiation system 110 to transmit pulse of electromagnetic radiation 116 through lens antenna 140 to form electromagnetic radiation beam 142 directed at composite sandwich panel 108 such that composite sandwich panel 108 is heated above the ambient temperature for composite sandwich panel 108.

Controller 114 also controls infrared detector system 112 to detect an amount of infrared radiation 122 generated in response to transmitting pulse of electromagnetic radiation 116 into composite sandwich panel 108 using time window 128. As depicted, time window 128 is selected to detect the amount of infrared radiation 122 when pulse of electromagnetic radiation 116 heats composite sandwich panel 108 such that infrared detector system 112 detects an amount of infrared radiation 122 in composite sandwich panel 108 when composite sandwich panel 108 is heated by pulse of electromagnetic radiation 116. The amount of infrared radiation 122 indicates a level of moisture 106 in composite sandwich panel 108.

In this illustrative example, time window 128 is selected to detect the amount of infrared radiation 122 in response to pulse of electromagnetic radiation 116 heating composite sandwich panel 108 such that a sensitivity of infrared detector system 112 is increased. This increase can occur by selecting width of time window 128 such that time window 128 encompasses all of pulse of electromagnetic radiation 116.

Controller 114 can be configured to control infrared detector system 112 to detect an amount of background infrared radiation 130 prior to electromagnetic radiation system 110 transmitting pulse of electromagnetic radiation 116. The amount of background infrared radiation 130 is the amount of infrared radiation 122 that is present without pulse of electromagnetic radiation 116 being directed into composite sandwich panel 108. Background infrared radiation 130 can be subtracted from the amount of infrared radiation 122 detected to determine infrared radiation 122 resulting from applying pulse of electromagnetic radiation 116 to composite sandwich panel 108.

Background infrared radiation 130 can be measured as an ambient temperature for composite sandwich panel 108. This ambient temperature may vary depending on the environment in which composite sandwich panel 108 is located. For example, composite sandwich panel 108 may be located inside the hangar, within an aircraft, or some other suitable location. Depending on the size of composite sandwich panel 108, a portion of the panel may be located inside of a building while another portion may be located outside of the building.

As depicted, controller 114 is configured to determine the level of moisture 106 in composite sandwich panel 108. In this example, the level of moisture 106 is determined using the amount of infrared radiation 122 detected and energy 120 for pulse of electromagnetic radiation 116 sent into composite sandwich panel 108.

Controller 114 is configured to generate visualization 134 of infrared radiation 122 for composite sandwich panel 108 using the amount of infrared radiation 122 detected by infrared detector system 112 within time window 128. Visualization 134 can be selected from at least one of a thermal map, a thermal image, or some other visualization of infrared radiation 122 for composite sandwich panel 108. Visualization 134 allows a user or other person to see where moisture 106 may be located within composite sandwich panel 108.

One or more solutions are present that overcome a problem with detecting moisture in porous materials. As a result, one or more technical solutions may provide a technical effect of determining a level of moisture 106 rather than merely detecting whether moisture 106 is present.

As a result, computer system 144 in this illustrative example operates as a special purpose computer system in which controller 114 in computer system 144 enables detecting a level of moisture 106 in porous material 104. In particular, controller 114 transforms computer system 144 into a special purpose computer system as compared to currently available general computer systems that do not have controller 114.

Figure 2:
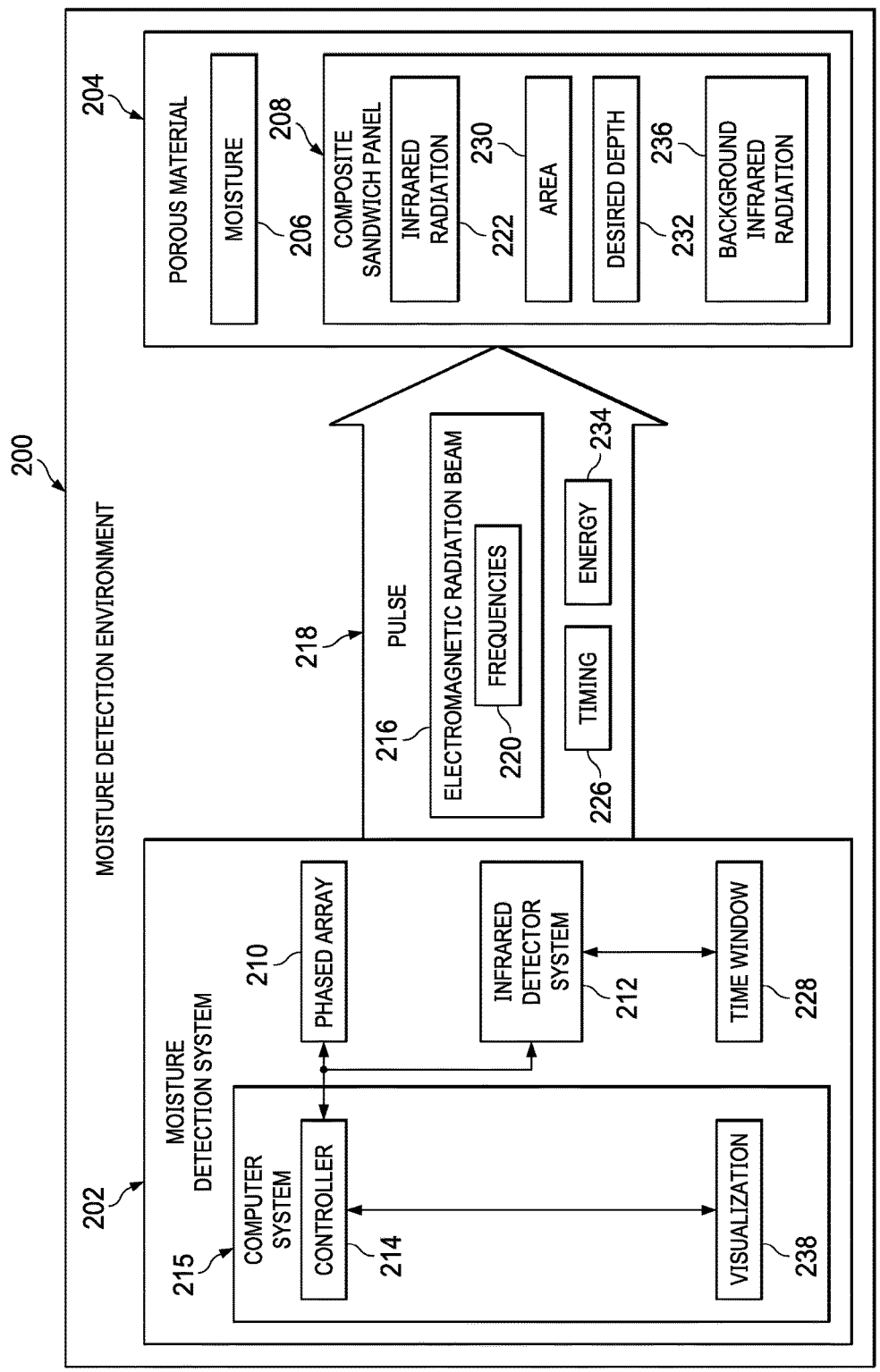
FIG. 2 is an illustration of a block diagram of a moisture detection environment in accordance with an illustrative example.

With reference to FIG. 2, another illustration of a block diagram of a moisture detection environment is depicted in accordance with an illustrative example. In this illustrative example, moisture detection environment 200 includes moisture detection system 202 configured to inspect porous material 204 for moisture 206. Moisture detection system 202 can be utilized to inspect porous material 204 for a level of moisture 206. As depicted, porous material 204 takes the form of composite sandwich panel 208.

In this illustrative example, moisture detection system 202 is comprised of a number of different components. As depicted, moisture detection system 202 includes phased array 210, infrared detector system 212, and controller 214.

As depicted, phased array 210 is an electronically scanned array and another manner in which a beam can be formed in addition to or in place of using a lens antenna. Phased array 210 transmits electromagnetic radiation beam 216 as pulse 218. In this illustrative example, phased array 210 can be an array of antennas controlled to create electromagnetic radiation beam 216, which may be radio frequency waves that can be electronically steered in different directions without physically moving the antennas in phased array 210.

In this illustrative example, pulse 218 of electromagnetic radiation beam 216 has a number of frequencies 220 selected from about 300 MHz to about 300 GHz. As depicted, controller 214 can select the number of frequencies 220 for pulse 218 of electromagnetic radiation beam 216 based on desired depth 232 at which pulse 218 of electromagnetic radiation beam 216 penetrates composite sandwich panel 208.

As depicted, infrared detector system 212 is configured to detect an amount of infrared radiation 222. Infrared detector system 212 may be implemented in a similar fashion to infrared detector system 112 in FIG. 1.

Controller 214 is in communication with phased array 210 and infrared detector system 212. Controller 214 is located in computer system 215. As depicted, controller 214 is configured to control phased array 210 to beam steer pulse 218 of electromagnetic radiation beam 216 transmitted from phased array 210 to composite sandwich panel 208. Controller 214 is also configured to synchronize timing 226 of pulse 218 of electromagnetic radiation beam 224 to heat composite sandwich panel 208 with time window 228 used by infrared detector system 212 to detect the amount of infrared radiation 222. Synchronizing timing 226 of pulse 218 also may include the scanning or movement of pulse 218 in addition to the duration of pulse 218 in these illustrative examples.

The synchronization increases the sensitivity in images of infrared radiation 222. For example, controller 214 is configured to control infrared detector system 212 to detect the amount of infrared radiation 222 in composite sandwich panel 208 within time window 228 when composite sandwich panel 208 is heated by pulse 218 of electromagnetic radiation beam 216.

In steering pulse 218 of electromagnetic radiation beam 216, controller 214 controls phased array 210 to beam steer pulse 218 to cover area 230 on composite sandwich panel 208. Controller 214 controls infrared detector system 212 to detect the amount of infrared radiation 222 radiating from area 230 within time window 228 when pulse 218 of electromagnetic radiation beam 216 heats area 230 on composite sandwich panel 208. In the illustrative example, time window 228 is selected to detect the amount of infrared radiation 222 in response to pulse 218 of electromagnetic radiation beam 216 heating composite sandwich panel 208 such that a sensitivity of infrared detector system 212 is increased.

With the use of phased array 210, the accuracy in determining area 230 increases as compared to using other types of radiation emission systems. With phased array 210, beam steering may be performed in a manner in which the location of the beam is more accurately known. As a result, determining energy 234 applied to area 230 is more accurate.

In this illustrative example, controller 214 is configured to determine the level of moisture 206 in composite sandwich panel 208 using the amount of infrared radiation 222 detected in area 230 and energy 234 in pulse 218 of electromagnetic radiation beam 216 sent into area 230 on composite sandwich panel 208.

Controller 214 can be configured to control infrared detector system 212 to detect an amount of background infrared radiation 236 prior to phased array 210 transmitting pulse 218 of electromagnetic radiation beam 216. The amount of background infrared radiation 236 is the amount of infrared radiation 222 that is present without pulse 218 of electromagnetic radiation beam 216 being directed into composite sandwich panel 208. Background infrared radiation 236 can be subtracted from the amount of infrared radiation 222 detected to determine infrared radiation 222 resulting from applying pulse 218 of electromagnetic radiation beam 216 to composite sandwich panel 208.

Additionally, controller 214 is configured to generate visualization 238 of the amount of infrared radiation 222 detected in composite sandwich panel 208. In this illustrative example, visualization 238 may be selected from at least one of a thermal image, a thermal map, or some other type of visualization. In the illustrative example, controller 214 is configured to generate a map of moisture 106 within composite sandwich panel 108 using visualization 238, such as a thermal map or a thermal image.

One or more solutions are present that overcome a problem with detecting moisture in porous structures such as composite sandwich panels. As a result, one or more technical solutions may provide an ability to detect moisture in a porous material including a composite sandwich panel. The controller controls the operation of an electromagnetic radiation system and an infrared detector system to detect a level of moisture in an area using a time window. The selection of the time window can increase the sensitivity of the infrared detector system.

As a result, computer system 215 in this illustrative example operates as a special purpose computer system in which controller 214 in computer system 215 enables controlling the operation of an electromagnetic radiation system and an infrared detector system to detect a level of moisture in an area using a time window. In particular, controller 114 transforms computer system 215 into a special purpose computer system, as compared to currently available general computer systems that do not have controller 214.

Controller 114 in FIG. 1 and controller 214 in FIG. 2, may be implemented in software, hardware, firmware, or a combination thereof. When software is used, the operations performed by these controllers may be implemented in program code configured to run on hardware, such as a processor unit. When firmware is used, the operations performed by controller 114 and controller 214 may be implemented in program code and data and stored in persistent memory to run on a processor unit. When hardware is employed, the hardware may include circuits that operate to perform the operations in controller 114 and controller 214.

The hardware can take a form selected from at least one of a circuit system, an integrated circuit, an application specific integrated circuit (ASIC), a programmable logic device, or some other suitable type of hardware configured to perform a number of operations. With a programmable logic device, the device can be configured to perform the number of operations. The device may be reconfigured at a later time or may be permanently configured to perform the number of operations. Programmable logic devices include, for example, a programmable logic array, a programmable array logic, a field programmable logic array, a field programmable gate array, and other suitable hardware devices. Additionally, the processes may be implemented in organic components integrated with inorganic components and may be comprised entirely of organic components excluding a human being. For example, the processes may be implemented as circuits in organic semiconductors.

As depicted, controller 114 is located in computer system 144. In this example, computer system 144 is a physical hardware system and includes one or more data processing systems. When more than one data processing system is present, those data processing systems are in communication with each other using a communications medium. The communications medium may be a network. The data processing systems may be selected from at least one of a computer, a server computer, a tablet, or some other suitable data processing system.

The illustration of moisture detection environment 100 in FIG. 1 and moisture detection environment 200 in FIG. 2 is not meant to imply physical or architectural limitations to the manner in which an illustrative example may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative example.

For example, composite sandwich panel 108 can have two cores between the first face sheet and the second face sheet. These two cores can be separated from each other by a layer similar to the face sheets. As another example, moisture detection system 102 can be used to detect a level of moisture 106 and other types of porous material 104 other than composite sandwich panel 108. Other types of porous material 104 may include, for example, a thermal protection system (TPS) on the exterior of a missile, a rocket, or a space vehicle. The thermal protection system is porous and can contain moisture.

Composite sandwich panel 108 and composite sandwich panel 208 can be utilized in other platforms other than an aerospace vehicle. The platform may be, for example, a mobile platform, a stationary platform, a land-based structure, an aquatic-based structure, and a space-based structure. More specifically, the platform may be a surface ship, a tank, a personnel carrier, a train, a space station, a satellite, a submarine, an automobile, a power plant, a bridge, a dam, a house, a manufacturing facility, a building, and other suitable platforms.

The power level can be selected to change the amount of heating in addition to or in place of selecting the wavelength. In one illustrative example, using a selected wavelength, and increasing the amplitude, a better representation of trapped moisture depth can be identified in porous material 104. By knowing the penetration depth from the selected wavelength and thermal dissipation, the trapped moisture depth can be determined. In other words, the depth at which moisture is present in porous material 104 can be determined. Further, the illustrative example can be applied to materials with voids or channels in which moisture is trapped but cannot escape.

Figure 3:
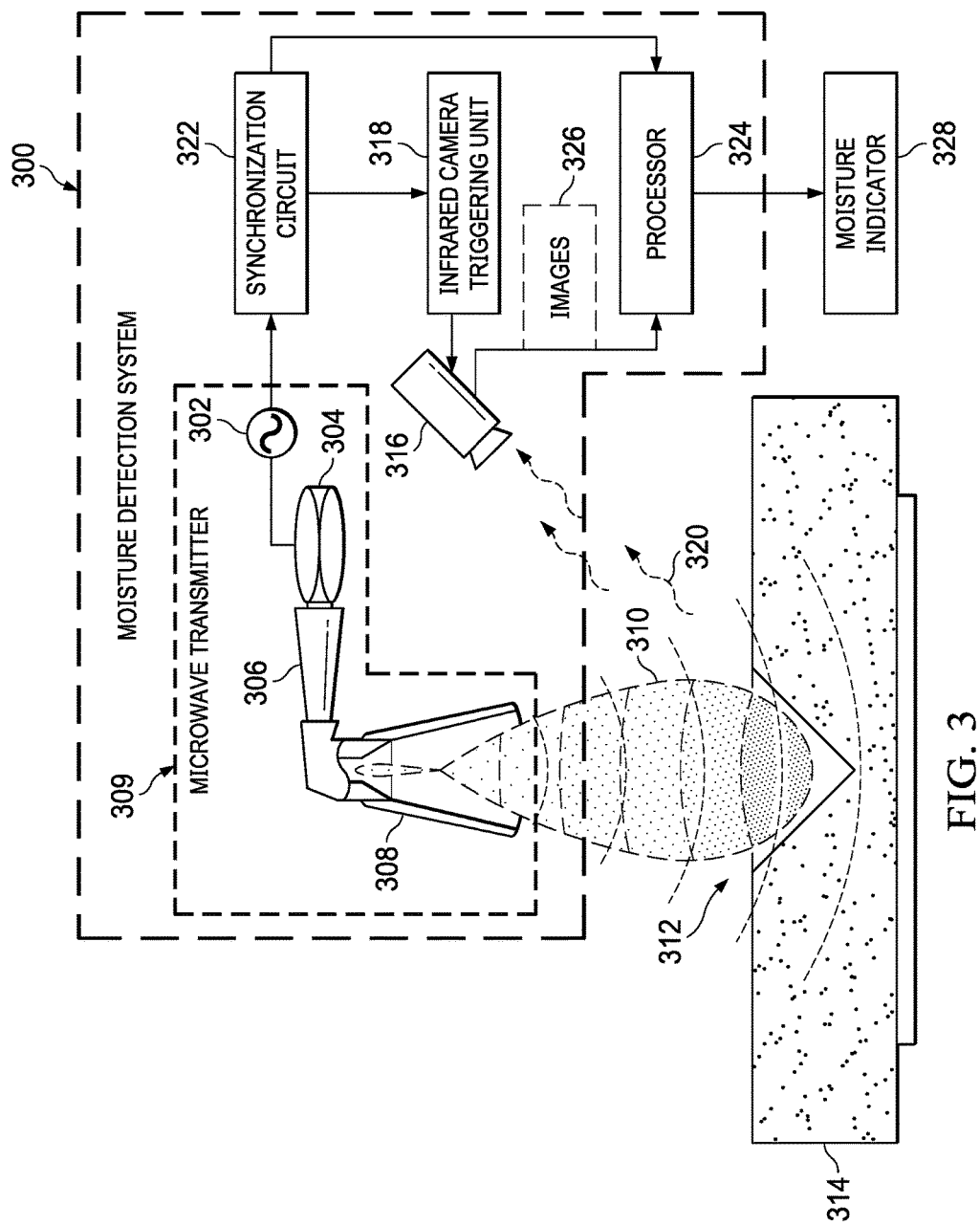
FIG. 3 is an illustration of a moisture detection system in accordance with the illustrative example.

With reference to FIG. 3, an illustration of a moisture detection system is depicted in accordance with an illustrative example. In the illustrative example, moisture detection system 300 is an example of one implementation for moisture detection system 102 shown in block form in FIG. 1.

As depicted, moisture detection system 300 includes radio frequency generator 302, magnetron 304, waveguide 306, and lens antenna 308. These components form microwave transmitter 309 and are examples of components that may be used in electromagnetic radiation system 110 shown in block form in FIG. 1.

As depicted, radio frequency generator 302 generates a radio frequency for the transmission of microwave beam 310. Magnetron 304 generates electromagnetic radiation in the form of microwaves in the social example. Waveguide 306 guides the microwaves generated by magnetron 304 through lens antenna 308. Lens antenna 308 causes the microwaves to be transmitted in of microwave beam 310. In the illustrative example, microwave beam 310 is directed at area 312 on porous material 314.

Moisture detection system 300 also includes infrared camera 316 and infrared camera triggering unit 318. These two components are examples of components that may be used to implement infrared detector system 112 shown in block form in FIG. 1 or infrared detector system 212 shown in block form in FIG. 2. As depicted, infrared camera 316 is positioned to detect infrared radiation 320 from area 312 in response to heating of porous material 314 by microwave beam 310.

As depicted, synchronization circuit 322 controls the operation of radio frequency generator 302 and infrared camera triggering unit 318. In this manner, synchronization circuit 322 can cause infrared camera 316 to detect infrared radiation 320 in the timing window based on when microwave beam 310 heats porous material 314.

In this illustrative example, processor 324 is configured to receive images 326 from infrared camera 316. Based on images 326 received, processor 324 generates moisture indicator 328. Moisture indicator 328 may be an indication of moisture that is present. In other illustrative examples, moisture indicator 328 may be a visualization such as visualization 134 shown in block form in FIG. 1 or visualization 238 shown in block form in FIG. 2.

As depicted in this example, processor 324 in moisture detection system 300 controls synchronization circuit 322 to select a timing window to synchronize the operation of transmitting microwave beam 310 with the detection of infrared radiation by infrared camera 316. Processor 324 is an example of a component that can be used to implement controller 114 shown in block form in FIG. 1 or controller 214 shown in block form in FIG. 2.

Figure 4:
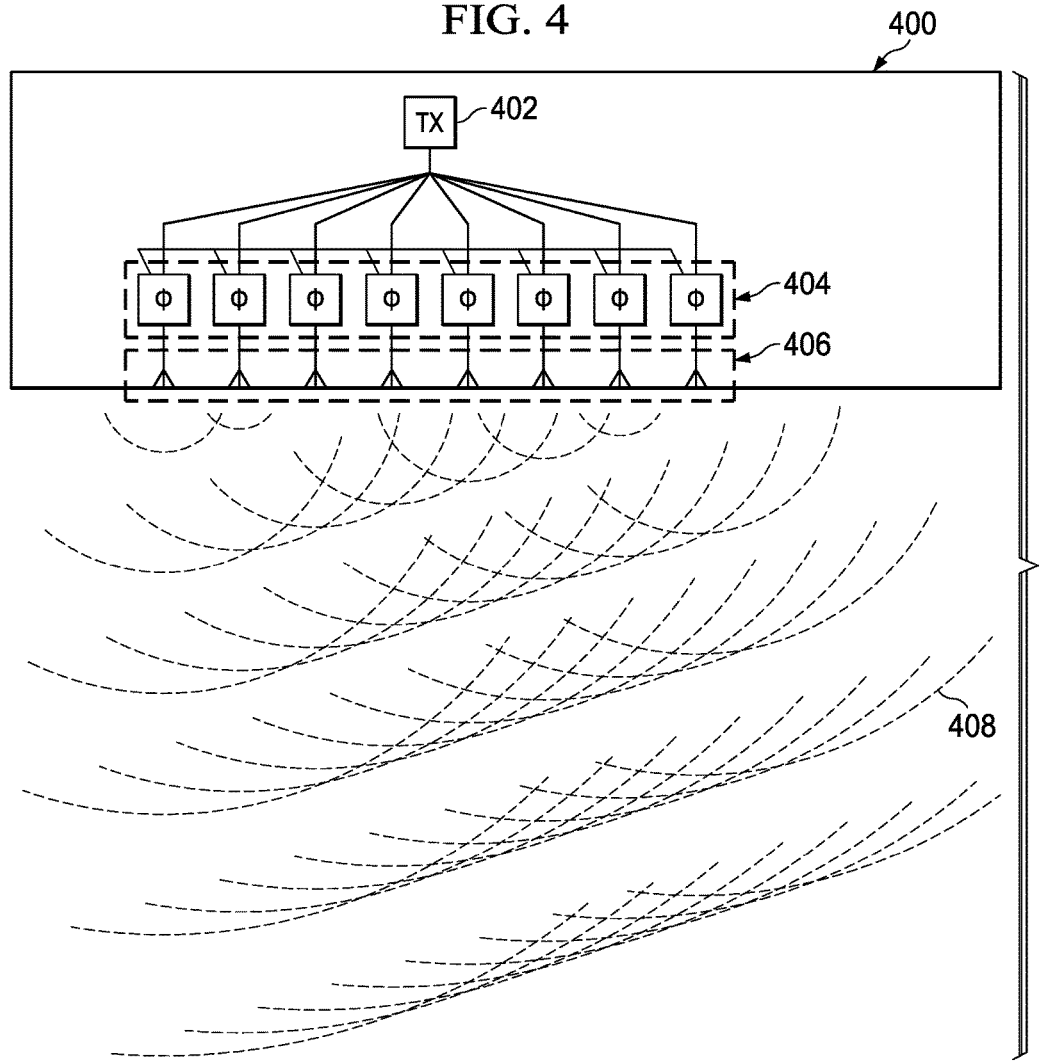
FIG. 4 is an illustration of a phased array in accordance with an illustrative example.

With reference next to FIG. 4, an illustration of a phased array is depicted in accordance with an illustrative example. In the depicted example, phased array 400 is an example of one implementation for phased array 210 shown in block form in FIG. 2. Phased array 400 can be used in place of microwave transmitter 309 in FIG. 3.

In the illustrative example, phased array 400 includes transmitters 402, phase shifters 404, and antenna elements 406. Phase shifters 404 can be controlled by a controller such as controller 114 shown in block form in FIG. 1, controller 214 shown in block form in FIG. 2, or processor 324 in FIG. 3. As depicted, phase shifters 404 can be controlled to cause antenna elements 406 to emit microwave beam 408 in a direction that can be changed electronically. In other words, microwave beam 408 is electronically steerable. In this manner, mechanical or moving parts are necessary to direct microwave beam 408.

The illustration of moisture detection system 300 in FIG. 3 and phased array in FIG. 4 are provided as examples of some implementations for components in moisture detection environment 100 shown in block form in FIG. 1 and moisture detection environment 200 shown in block form in FIG. 2. These examples are not meant to limit the manner in which other illustrative examples may be implemented. For example, although eight transmitters are shown for transmitters 402, other numbers of transmitters may be used. For example, 11, 27, 45, or some other suitable number of transmitters may be used in other illustrative examples.

Figure 5:
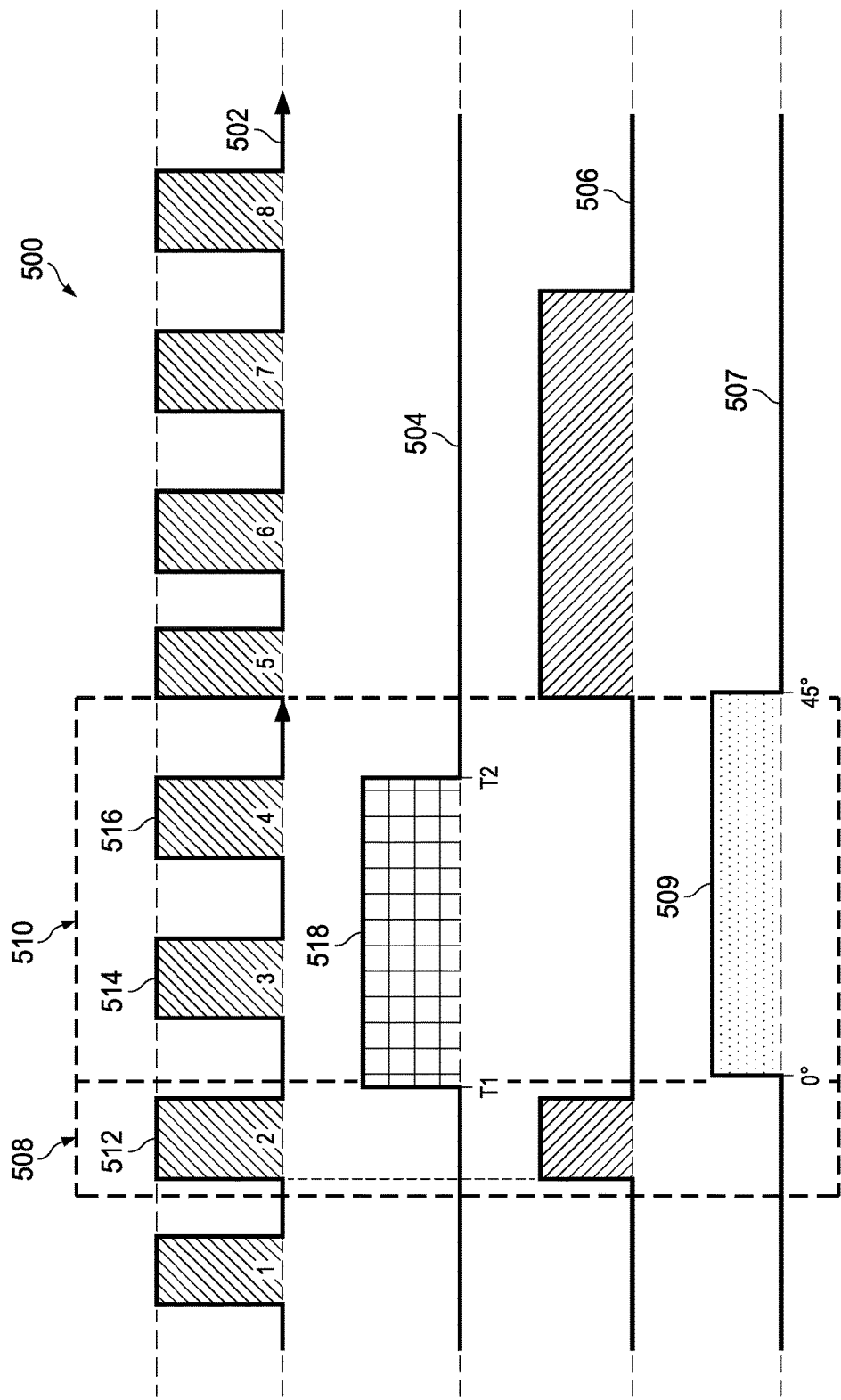
FIG. 5 is an illustration of a timing diagram in accordance with an illustrative example.

Turning next to FIG. 5, an illustration of a timing diagram is depicted in accordance with an illustrative example. Timing diagram 500 includes infrared camera frames graph 502, pulse graph 504, image storage graph 506, and steering graph 507.

Infrared camera frames graph 502 is a graph showing the timing of frames during which infrared radiation is detected by an infrared camera. Each frame represents a period of time during which photons are detected for generating an image of infrared radiation in this illustrative example.

Pulse graph 504 is a graph showing the timing of when electromagnetic radiation pulse is emitted by the electromagnetic radiation system and the duration during the pulse of the electromagnetic radiation beam. The depth at which the electromagnetic radiation pulse can be selected based on the frequency. Increasing the frequency increases the penetration, while decreasing the frequency reduces the penetration of the pulse of the electromagnetic radiation beam into the porous material.

Image storage graph 506 is a graph showing the time during which the frames generated by infrared camera are stored. When data is stored, the sensors in the infrared camera are not detecting photons.

Steering graph 507 is a graph showing the steering of the electromagnetic radiation pulse. In this example, steering signal 509 shows the pulse of electromagnetic radiation being steered from about 0° to about 45° to cover an area of interest.

As depicted, two time windows are present, time window 508 and time window 510. In this illustrative example, time window 508 is a period of time during which frame 512 is generated and stored. Time window 508 is used to identify background infrared radiation. This background infrared radiation may reflect the ambient temperature of the environment in which the porous material is located. Time window 510 is a period of time during which frame 514 and frame 516 are detected by the infrared camera.

Synchronization is performed such that these frames occur when pulse 518 in pulse graph 504 occurs. Pulse 518 represents the pulse of electromagnetic radiation, such as microwaves, that are directed into the porous material.

The timing of pulse 518 is such that frame 514 and frame 516 detect as much infrared radiation as possible. During time window 510, the infrared radiation increases from when pulse 518 begins at time T1 and ends at time T2. The selection of time window 510 along with the transmission of pulse 518 within time window 510 allows for an infrared camera to detect the maximum amount of infrared radiation caused by pulse 518, thus increasing the sensitivity of the infrared camera. In this manner, the sensitivity of the infrared camera may be increased through the selection of time window 510 to include as much of pulse 518 as possible.

Further, the length of pulse 518 and the size of time window 510 is selected to cover the time during which photons are detected by the infrared camera prior to transferring signals from the sensors in the infrared camera for storage as an image. As a result, continued transmission of microwaves does not occur while data is read from the sensors in the infrared camera.

Figures 6, 7:
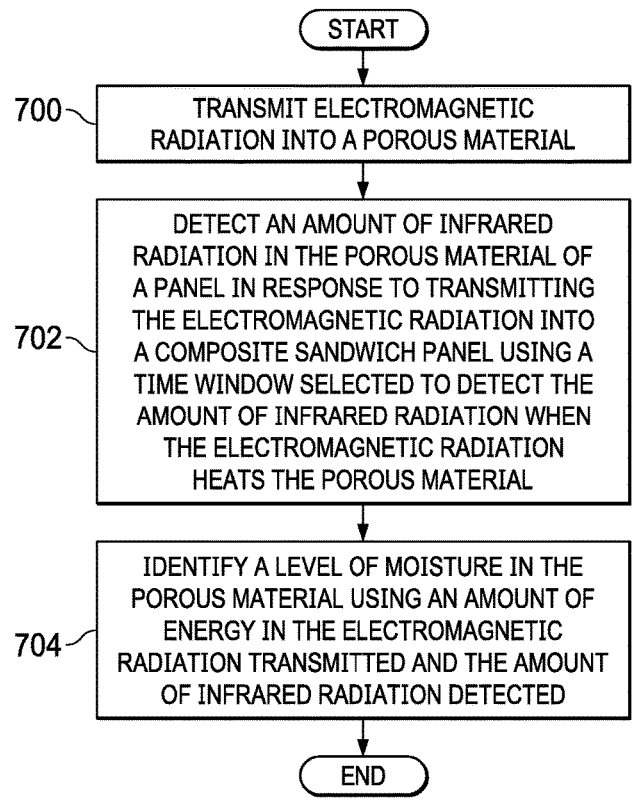
FIG. 6 is an illustration of a table of material parameters in accordance with an illustrative example.
FIG. 7 is an illustration of a flowchart of a process for detecting moisture in a porous material in accordance with an illustrative example.

With reference to FIG. 6, an illustration of a table of material parameters is depicted in accordance with an illustrative example. Table 600 illustrates parameters used in selecting a desired depth of penetration for electromagnetic radiation. In the illustrative example, entry 602 is for an example porous material, such as a core in a composite sandwich panel. The panel has a decorative laminate that is about 2 mm thick, a skin panel that is about 1 mm thick, and a honeycomb and foam core that is about 25 mm thick.

Column 604 indicates electrical conductivity, column 606 is magnetic permeability, column 608 is frequency, and column 610 identifies depth of penetration. The depth in column 610 is calculated as follows:

$$\delta \approx \frac{1}{\sqrt{\pi f \mu \sigma}}$$

where δ is standard depth of penetration (mm); π is 3.14; f is test frequency (Hz); μ is magnetic permeability (H/mm); and σ is electrical conductivity (% IACS).

In this depicted example, table 600 provides a depth of penetration for the core in this example. Generally, the depth of penetration increases as the frequency increases. All of the properties of the porous material being inspected can be taken into account in determining the depth of penetration.

For example, when the porous material is a composite sandwich core, the decorative laminate, the panel skin, as well as the honeycomb and foam core may also be taken into account to obtain a more accurate depth of penetration.

Turning next to FIG. 7, an illustration of a flowchart of a process for detecting moisture in a porous material is depicted in accordance with an illustrative example. The process illustrated in FIG. 7 can be implemented in moisture detection system 102 shown in block form in FIG. 1. This process may be implemented in at least one of hardware or software. When software in the form of program code is used, the program code can be run by a processor unit to perform the different operations.

The process begins by transmitting electromagnetic radiation into a porous material (operation 700). The electromagnetic radiation beam in operation 700 has a number of wavelengths that is absorbed by water molecules. In this example, selecting the number of frequencies for the electromagnetic radiation is based on a desired depth at which a pulse of electromagnetic radiation penetrates the composite sandwich panel.

The process detects an amount of infrared radiation in the porous material of a panel in response to transmitting the electromagnetic radiation into a composite sandwich panel using a time window selected to detect the amount of infrared radiation when the electromagnetic radiation heats the porous material (operation 702). The process identifies a level of moisture in the porous material using an amount of energy in the electromagnetic radiation transmitted and the amount of infrared radiation detected (operation 704). The process terminated thereafter.

Figure 8:
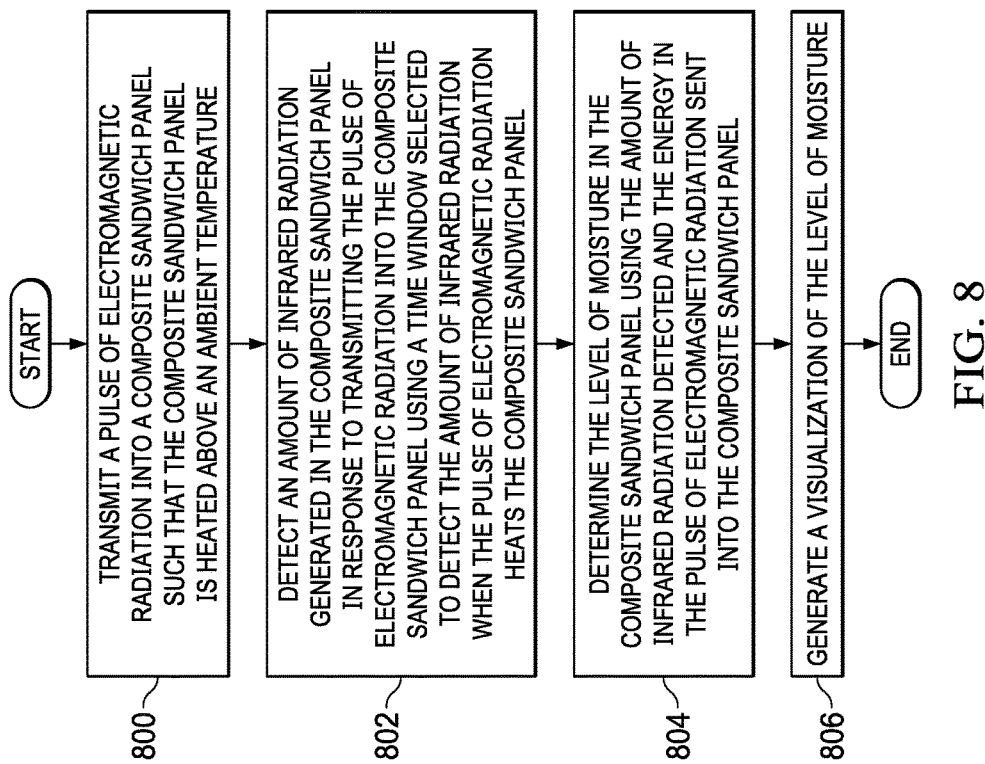
FIG. 8 is an illustration of a flowchart of a process for detecting moisture in a composite sandwich panel for an aerospace vehicle in accordance with an illustrative example.

With reference next to FIG. 8, an illustration of a flowchart of a process for detecting moisture in a composite sandwich panel for an aerospace vehicle is depicted in accordance with an illustrative example. This process may be implemented in at least one of hardware or software. When software in the form of program code is used, the program code can be run by a processor unit to perform the different operations in the process.

The process begins by transmitting a pulse of electromagnetic radiation into a composite sandwich panel such that the composite sandwich panel is heated above an ambient temperature (operation 800). The process detects an amount of infrared radiation generated in the composite sandwich panel in response to transmitting the pulse of electromagnetic radiation into the composite sandwich panel using a time window selected to detect the amount of infrared radiation when the pulse of electromagnetic radiation heats the composite sandwich panel (operation 802). The amount of infrared radiation detected indicates an amount of moisture in the composite sandwich panel.

The process determines the level of moisture in the composite sandwich panel using the amount of infrared radiation detected and the energy in the pulse of electromagnetic radiation sent into the composite sandwich panel (operation 804). The process then generates a visualization of the level of moisture (operation 806). The process terminates thereafter.

The visualization may be selected from at least one of a thermal image, a thermal map, or some other representation. This visualization may be used to identify locations where moisture is present. Further, the visualization may indicate the depth at which the moisture is present in those locations.

Based on the level of moisture detected, an action can be performed with respect to the composite sandwich panel. This action can be selected from reworking or replacing the composite sandwich panel. The reworking may include, for example, sending additional electromagnetic radiation into the composite sandwich panel in an effort to reduce the moisture in the composite sandwich panel. Other moisture reduction techniques also may be used. Thermal or infrared heating may be employed.

Figure 9:
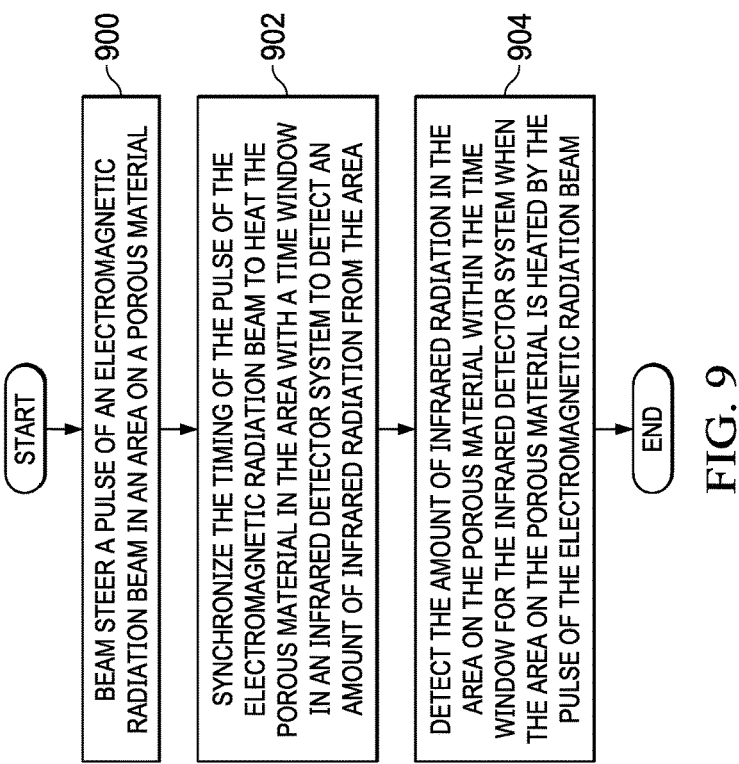
FIG. 9 is an illustration of a flowchart of a process for detecting moisture in a porous material in accordance with an illustrative example.

Turning next to FIG. 9, an illustration of a flowchart of a process for detecting moisture in a porous material is depicted in accordance with an illustrative example. The process illustrated in FIG. 9 can be implemented in moisture detection system 202 shown in block form in FIG. 2. This process may be implemented in at least one of hardware or software. When software in the form of program code is used, the program code can be run by a processor unit to perform the different operations.

The process beings by beam steering a pulse of an electromagnetic radiation beam in an area on a porous material (operation 900). The beam steering moves the pulse of the electromagnetic radiation beam across the area to cover the area. The pulse of the electromagnetic radiation beam has a number of wavelengths that are absorbed by water molecules.

The process synchronizes the timing of the pulse of the electromagnetic radiation beam to heat the porous material in the area with a time window in an infrared detector system to detect an amount of infrared radiation from the area (operation 902). The process detects the amount of infrared radiation in area on the porous material within the time window for the infrared detector system when the area on the porous material is heated by the pulse of the electromagnetic radiation beam (operation 904). The process terminates thereafter. The amount of infrared radiation indicates a level of moisture in the porous material.

Figure 10:
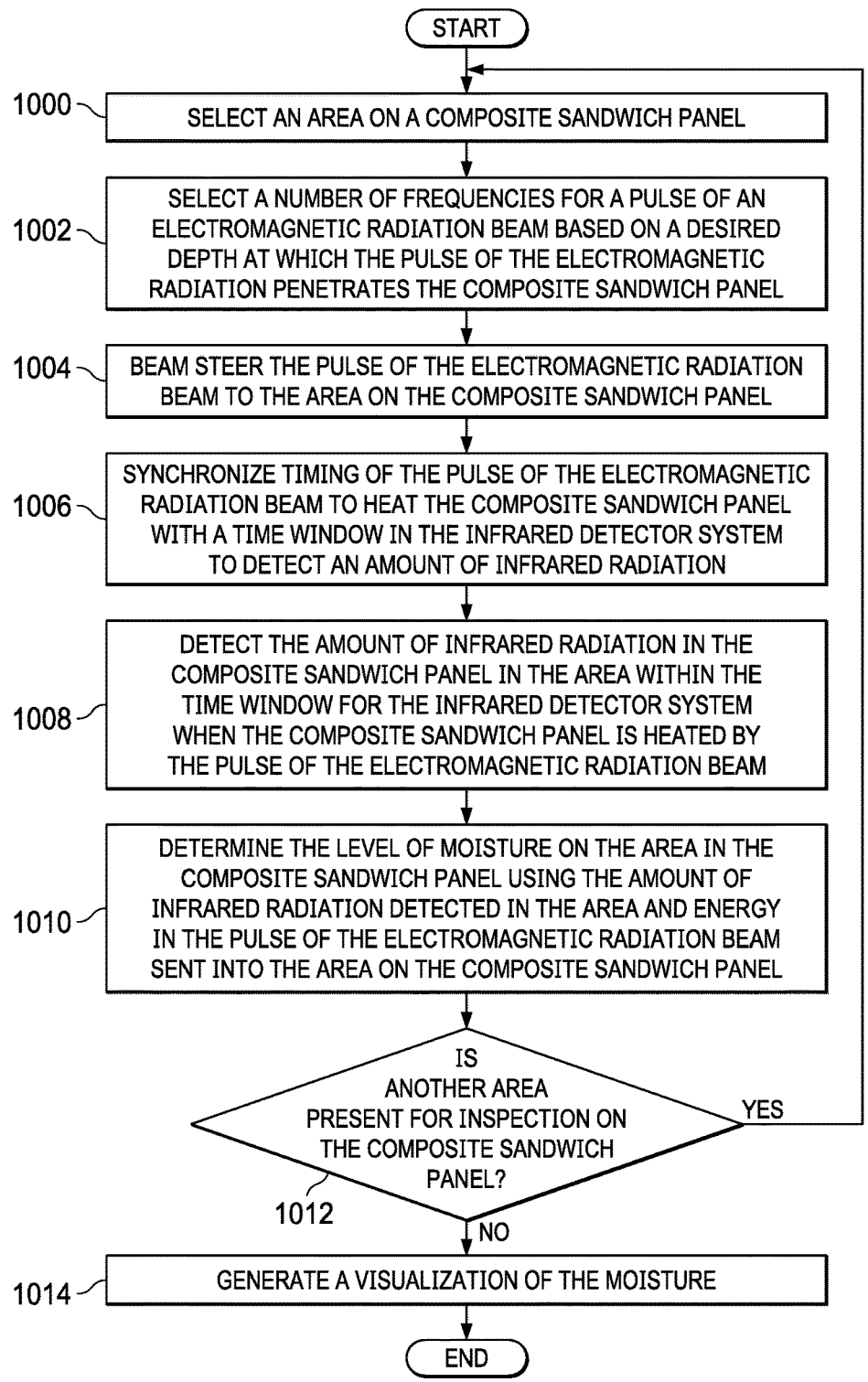
FIG. 10 is an illustration of a flowchart of a process for detecting moisture in detecting moisture in a composite sandwich panel for an aerospace vehicle in accordance with an illustrative example.

With reference to FIG. 10, an illustration of a flowchart of a process for detecting moisture in a composite sandwich panel for an aerospace vehicle is depicted in accordance with an illustrative example. The process illustrated in FIG. 10 can be implemented in moisture detection system 202 shown in block form in FIG. 2. This process may be implemented in at least one of hardware or software. When software in the form of program code is used, the program code can be run by a processor unit to perform the different operations. The process begins by selecting an area on a composite sandwich panel (operation 1000). This area can be some of or all of the composite sandwich panel. The process selects a number of frequencies for a pulse of an electromagnetic radiation beam based on a desired depth at which the pulse of the electromagnetic radiation penetrates the composite sandwich panel (operation 1002). The pulse of the electromagnetic radiation beam has a number of wavelengths that is absorbed by water molecules.

The process beam steers the pulse of the electromagnetic radiation beam to the area on the composite sandwich panel (operation 1004). The steering can be performed such that the entire area is covered during a pulse or multiple pulses may be used to cover the area. The process synchronizes timing of the pulse of the electromagnetic radiation beam to heat the composite sandwich panel with a time window in the infrared detector system to detect an amount of infrared radiation (operation 1006).

The process detects the amount of infrared radiation in the composite sandwich panel in the area within the time window for the infrared detector system when the composite sandwich panel is heated by the pulse of the electromagnetic radiation beam (operation 1008). The amount of infrared radiation indicates a level of moisture in the composite sandwich panel.

The process determines the level of moisture in the area on the composite sandwich panel using the amount of infrared radiation detected in the area and energy in the pulse of the electromagnetic radiation beam sent into the area on the composite sandwich panel (operation 1010).

A determination is made as to whether another area is present for inspection on the composite sandwich panel (operation 1012). If another area is present, the process returns to operation 1000. Otherwise, the process generates a visualization of the moisture (operation 1014). The process terminates thereafter.

The visualization can be a thermal image or a map of the infrared radiation for the porous material using the energy in the pulse of the electromagnetic radiation beam and the amount of infrared radiation detected by the infrared detector system in the area within the time window.

Figure 11:
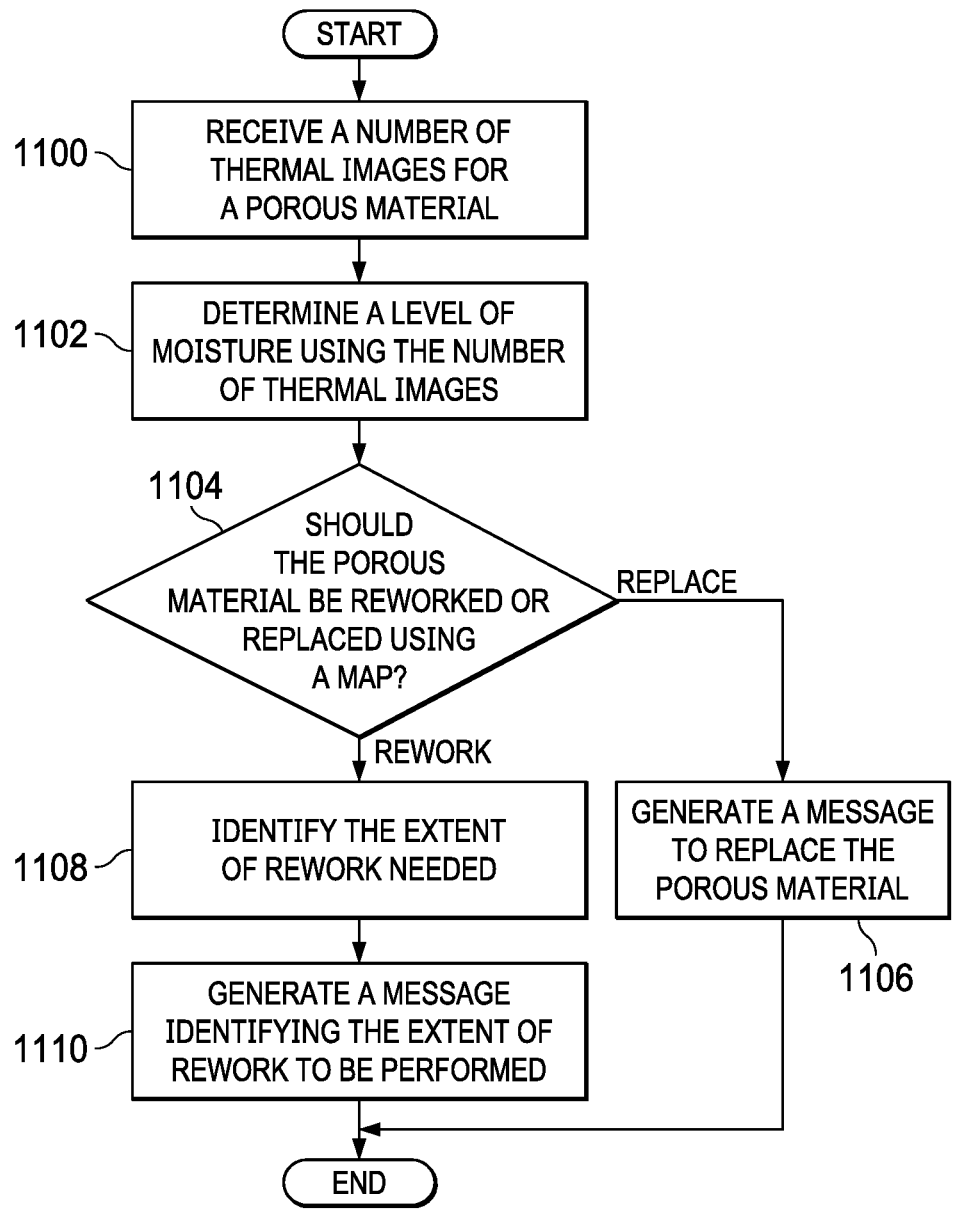
FIG. 11 is an illustration of a flowchart of a process for managing actions performed with respect to a porous material in response to detecting the level moisture in accordance with an illustrative example.

With reference to FIG. 11, an illustration of a flowchart of a process for managing actions performed with respect to a porous material in response to detecting a level of moisture is depicted in accordance with an illustrative example. The process illustrated in FIG. 10 can be implemented in moisture detection system 202 shown in block form in FIG. 2. This process may be implemented in at least one of hardware or software. When software in the form of program code is used, the program code can be run by a processor unit to perform the different operations.

The process begins by receiving a number of thermal images for a porous material (operation 1100). In this illustrative example, the number of thermal images may be for one or more areas of interest in the porous material. The process determines a level of moisture using the number of thermal images (operation 1102).

The process determines whether the porous material should be reworked or replaced using a map (operation 1104). If the porous material should be replaced, the process generates a message to replace the porous material (operation 1106). The process terminates thereafter.

With reference again to operation 1104, if a determination is made that the porous material should be reworked, the process identifies the extent of rework needed (operation 1108). This extent can be graphically identified on the map or with other instructions.

Further, the extent of rework also may identify the operations that should be performed to rework the porous material. This rework can include heating or other actions. For example, the rework may include removing a skin panel or decorative laminate from a composite sandwich panel, heating the composite sandwich panel, and then replacing the skin panel or decorative.

The process then generates a message identifying the extent of rework to be performed (operation 1110). The process terminates thereafter.

The flowcharts and block diagrams in the different depicted examples illustrate the architecture, functionality, and operation of some possible implementations of apparatuses and methods in an illustrative example. In this regard, each block in the flowcharts or block diagrams may represent at least one of a module, a segment, a function, or a portion of an operation or step. For example, one or more of the blocks may be implemented as program code, hardware, or a combination of the program code and hardware. When implemented in hardware, the hardware may, for example, take the form of integrated circuits that are manufactured or configured to perform one or more operations in the flowcharts or block diagrams. When implemented as a combination of program code and hardware, the implementation may take the form of firmware. Each block in the flowcharts or the block diagrams may be implemented using special purpose hardware systems that perform the different operations or combinations of special purpose hardware and program code run by the special purpose hardware.

In some alternative implementations of an illustrative example, the function or functions noted in the blocks may occur out of the order noted in the figures. For example, in some cases, two blocks shown in succession may be performed substantially concurrently, or the blocks may sometimes be performed in the reverse order, depending upon the functionality involved. Also, other blocks may be added in addition to the illustrated blocks in a flowchart or block diagram.

Figure 12:
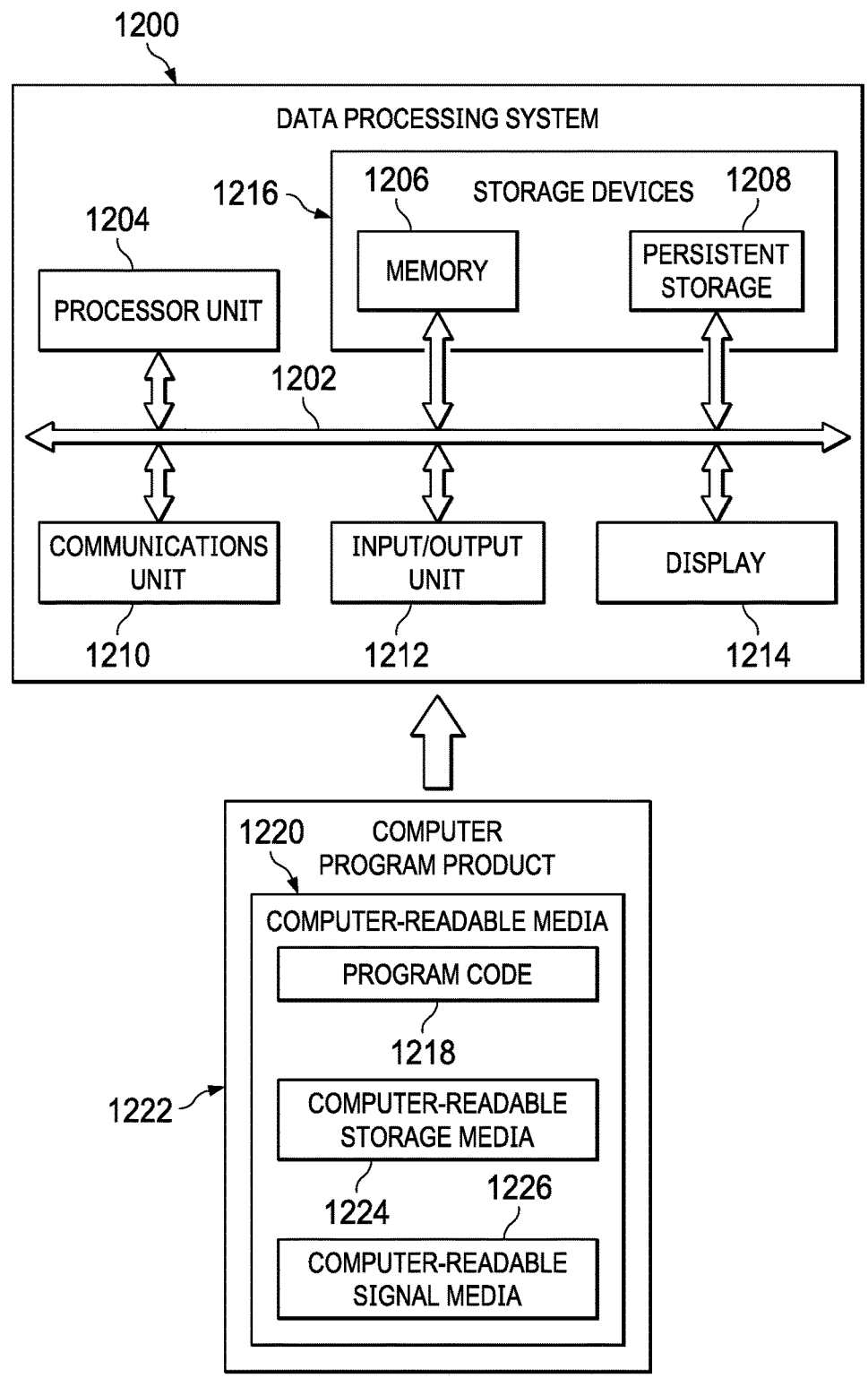
FIG. 12 is an illustration of a block diagram of a data processing system in accordance with an illustrative example.

Turning now to FIG. 12, an illustration of a block diagram of a data processing system is depicted in accordance with an illustrative example. Data processing system 1200 may be used to implement computer system 144 shown in block form in FIG. 1 and computer system 215 shown in block form in FIG. 2. In this illustrative example, data processing system 1200 includes communications framework 1202, which provides communications between processor unit 1204, memory 1206, persistent storage 1208, communications unit 1210, input/output (I/O) unit 1212, and display 1214. In this example, communications framework 1202 may take the form of a bus system.

Processor unit 1204 serves to execute instructions for software that may be loaded into memory 1206. Processor unit 1204 may be a number of processors, a multi-processor core, or some other type of processor, depending on the particular implementation.

Memory 1206 and persistent storage 1208 are examples of storage devices 1216. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 1216 may also be referred to as computer-readable storage devices in these illustrative examples. Memory 1206, in these examples, may be, for example, a random-access memory or any other suitable volatile or non-volatile storage device. Persistent storage 1208 may take various forms, depending on the particular implementation.

For example, persistent storage 1208 may contain one or more components or devices. For example, persistent storage 1208 may be a hard drive, a solid state hard drive, a flash memory, a rewritable optical disk, a rewritable magnetic tape, or some combination of the above. The media used by persistent storage 1208 also may be removable. For example, a removable hard drive may be used for persistent storage 1208.

Communications unit 1210, in these illustrative examples, provides for communications with other data processing systems or devices. In these illustrative examples, communications unit 1210 is a network interface card.

Input/output unit 1212 allows for input and output of data with other devices that may be connected to data processing system 1200. For example, input/output unit 1212 may provide a connection for user input through at least one of a keyboard, a mouse, or some other suitable input device. Further, input/output unit 1212 may send output to a printer. Display 1214 provides a mechanism to display information to a user.

Instructions for at least one of the operating system, applications, or programs may be located in storage devices 1216, which are in communication with processor unit 1204 through communications framework 1202. The processes of the different examples may be performed by processor unit 1204 using computer-implemented instructions, which may be located in a memory, such as memory 1206.

These instructions are referred to as program code, computer usable program code, or computer-readable program code that may be read and executed by a processor in processor unit 1204. The program code in the different examples may be embodied on different physical or computer-readable storage media, such as memory 1206 or persistent storage 1208.

Program code 1218 is located in a functional form on computer-readable media 1220 that is selectively removable and may be loaded onto or transferred to data processing system 1200 for execution by processor unit 1204. Program code 1218 and computer-readable media 1220 form computer program product 1222 in these illustrative examples. In one example, computer-readable media 1220 may be computer-readable storage media 1224 or computer-readable signal media 1226.

In these illustrative examples, computer-readable storage media 1224 is a physical or tangible storage device used to store program code 1218 rather than a medium that propagates or transmits program code 1218.

Alternatively, program code 1218 may be transferred to data processing system 1200 using computer-readable signal media 1226. Computer-readable signal media 1226 may be, for example, a propagated data signal containing program code 1218. For example, computer-readable signal media 1226 may be at least one of an electromagnetic signal, an optical signal, or any other suitable type of signal. These signals may be transmitted over at least one of communications links, such as wireless communications links, optical fiber cable, coaxial cable, a wire, or any other suitable type of communications link.

The different components illustrated for data processing system 1200 are not meant to provide architectural limitations to the manner in which different examples may be implemented. The different illustrative examples may be implemented in a data processing system including components in addition to or in place of those illustrated for data processing system 1200. Other components shown in FIG. 12 can be varied from the illustrative examples shown. The different examples may be implemented using any hardware device or system capable of running program code 1218.

Figure 14:
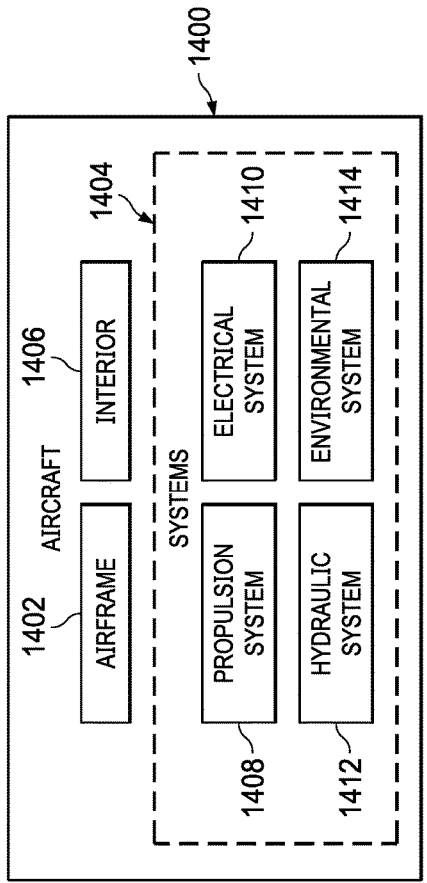
FIG. 14 is an illustration of a block diagram of an aircraft in which an illustrative example may be implemented.
Figure 13:
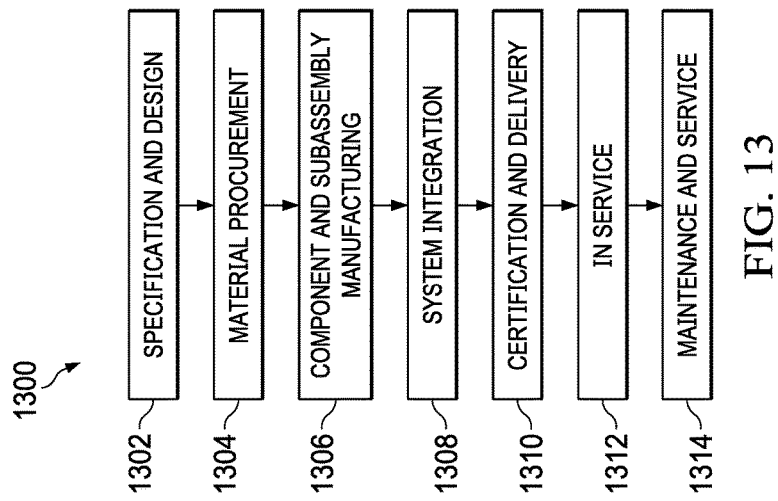
FIG. 13 is an illustration of a block diagram of an aircraft manufacturing and service method in accordance with an illustrative example.

Illustrative examples of the disclosure may be described in the context of aircraft manufacturing and service method 1300 as shown in FIG. 13 and aircraft 1400 as shown in FIG. 14. Turning first to FIG. 13, an illustration of a block diagram of an aircraft manufacturing and service method is depicted in accordance with an illustrative example. During pre-production, aircraft manufacturing and service method 1300 may include specification and design 1302 of aircraft 1400 in FIG. 14 and material procurement 1304.

During production, component and subassembly manufacturing 1306 and system integration 1308 of aircraft 1400 takes place. Thereafter, aircraft 1400 may go through certification and delivery 1310 in order to be placed in service 1312. While in service 1312 by a customer, aircraft 1400 is scheduled for routine maintenance and service 1314, which may include modification, reconfiguration, refurbishment, and other maintenance or service.

Each of the processes of aircraft manufacturing and service method 1300 may be performed or carried out by a system integrator, a third party, an operator, or some combination thereof. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 14, an illustration of a block diagram of an aircraft is depicted in which an illustrative example may be implemented. In this example, aircraft 1400 is produced by aircraft manufacturing and service method 1300 in FIG. 13 and may include airframe 1402 with plurality of systems 1404 and interior 1406. Examples of systems 1404 include one or more of propulsion system 1408, electrical system 1410, hydraulic system 1412, and environmental system 1414. Any number of other systems may be included. Although an aerospace example is shown, different illustrative examples may be applied to other industries, such as the automotive industry.

Apparatuses and methods embodied herein may be employed during at least one of the stages of aircraft manufacturing and service method 1300 in FIG. 13.

In one illustrative example, components or subassemblies produced in component and subassembly manufacturing 1306 in FIG. 13 may be fabricated or manufactured in a manner similar to components or subassemblies produced while aircraft 1400 is in service 1312 in FIG. 13. Moisture detection system 102 shown in block form in FIG. 1 and moisture detection system 202 shown in block form in FIG. 2 may be utilized to inspect porous materials for components or subassemblies produced during component and subassembly manufacturing 1306 or while aircraft is in service 1312.

As yet another example, one or more apparatus examples, method examples, or a combination thereof may be utilized during production stages, such as component and subassembly manufacturing 1306 and system integration 1308 in FIG. 13. Moisture detection system 102 in FIG. 1 and moisture detection system 202 in FIG. 2 may be utilized to inspect porous materials for components or subassemblies during component and subassembly manufacturing 1306, system integration 1308, and certification and delivery 1310. These inspections may be performed prior to delivery of aircraft 1400 to a customer. In other illustrative examples, these inspections may be performed during maintenance and service 1314.

One or more apparatus examples, method examples, or a combination thereof may be utilized while aircraft 1400 is in service 1312, during maintenance and service 1314 in FIG. 13, or both. The use of a number of the different illustrative examples may substantially expedite the assembly of aircraft 1400, reduce the cost of aircraft 1400, or both expedite the assembly of aircraft 1400 and reduce the cost of aircraft 1400.

Figure 15:
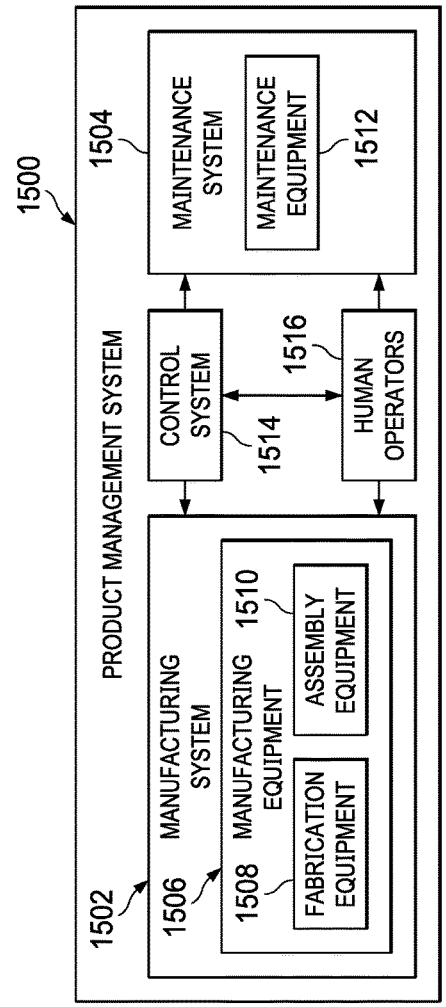
FIG. 15 is an illustration of a block diagram of a product management system in accordance with an illustrative example.

Turning now to FIG. 15, an illustration of a block diagram of a product management system is depicted in accordance with an illustrative example. Product management system 1500 is a physical hardware system. In this illustrative example, product management system 1500 may include at least one of manufacturing system 1502 or maintenance system 1504.

Manufacturing system 1502 is configured to manufacture products, such as aircraft 1400 in FIG. 14. As depicted, manufacturing system 1502 includes manufacturing equipment 1506. Manufacturing equipment 1506 includes at least one of fabrication equipment 1508 or assembly equipment 1510. Manufacturing equipment 1506 also may include moisture detection system 102 in FIG. 1 and moisture detection system 202 in FIG. 2 for use in inspecting components manufactured by manufacturing equipment 1506

Fabrication equipment 1508 is equipment that may be used to fabricate components for parts used to form aircraft 1400. For example, fabrication equipment 1508 may include machines and tools. These machines and tools may be at least one of a drill, a hydraulic press, a furnace, a mold, a composite tape laying machine, a vacuum system, a lathe, or other suitable types of equipment. Fabrication equipment 1508 may be used to fabricate at least one of metal parts, composite parts, semiconductors, circuits, fasteners, ribs, skin panels, spars, antennas, or other suitable types of parts.

Assembly equipment 1510 is equipment used to assemble parts to form aircraft 1400. In particular, assembly equipment 1510 may be used to assemble components and parts to form aircraft 1400. Assembly equipment 1510 also may include machines and tools. These machines and tools may be at least one of a robotic arm, a crawler, a faster installation system, a rail-based drilling system, or a robot. Assembly equipment 1510 may be used to assemble parts such as seats, horizontal stabilizers, wings, engines, engine housings, landing gear systems, and other parts for aircraft 1400.

In this illustrative example, maintenance system 1504 includes maintenance equipment 1512. Maintenance equipment 1512 may include any equipment needed to perform maintenance on aircraft 1400. Maintenance equipment 1512 may include tools for performing different operations on parts on aircraft 1400. These operations may include at least one of disassembling parts, refurbishing parts, inspecting parts, reworking parts, manufacturing replacement parts, or other operations for performing maintenance on aircraft 1400. These operations may be for routine maintenance, inspections, upgrades, refurbishment, or other types of maintenance operations.

In the illustrative example, maintenance equipment 1512 may include ultrasonic inspection devices, x-ray imaging systems, vision systems, drills, crawlers, and other suitable device. For example, maintenance equipment 1512 also may include moisture detection system 102 shown in block form in FIG. 1 and moisture detection system 202 shown in block form in FIG. 2 for use in inspecting porous materials such as a composite sandwich panel or other types of suitable components. In some cases, maintenance equipment 1512 may include fabrication equipment 1508, assembly equipment 1510, or both to produce and assemble parts that may be needed for maintenance.

Product management system 1500 also includes control system 1514. Control system 1514 is a hardware system and may also include software or other types of components. Control system 1514 is configured to control the operation of at least one of manufacturing system 1502 or maintenance system 1504. In particular, control system 1514 may control the operation of at least one of fabrication equipment 1508, assembly equipment 1510, or maintenance equipment 1512.

The hardware in control system 1514 may be using hardware that may include computers, circuits, networks, and other types of equipment. The control may take the form of direct control of manufacturing equipment 1506. For example, robots, computer-controlled machines, and other equipment may be controlled by control system 1514. In other illustrative examples, control system 1514 may manage operations performed by human operators 1516 in manufacturing or performing maintenance on aircraft 1400 in FIG. 14. For example, control system 1514 may assign tasks, provide instructions, display models, or perform other operations to manage operations performed by human operators 1516. In these illustrative examples, may be implemented in control system 1514 to manage at least one of the manufacturing or maintenance of aircraft 1400.

For example, management may include inspections performed using moisture detection system 102 shown in block form in FIG. 1 and moisture detection system 202 shown in block form in FIG. 2. Based on the level of moisture detected, control system 1514 may perform actions such as initiating rework, replacement, or other actions with respect to the inspected components. Further, the moisture detection system may generate a map of moisture from the infrared radiation detected within a structure such as a composite sandwich panel. The amount of infrared radiation in a thermal image correlates to the amount of moisture present in the structure.

This map may be used to determine whether rework or replacement of a component should occur. Further, when rework occurs, the map may also be used to determine whether rework should be performed. This determination may be turned into instructions that are used to control other equipment or sent to human operator 1516.

In the different illustrative examples, human operators 1516 may operate or interact with at least one of manufacturing equipment 1506, maintenance equipment 1512, or control system 1514. This interaction may be performed to manufacture aircraft 1400.

Of course, product management system 1500 may be configured to manage other products other than aircraft 1400. Although product management system 1500 has been described with respect to manufacturing in the aerospace industry, product management system 1500 may be configured to manage products for other industries. For example, product management system 1500 can be configured to manufacture products for the automotive industry as well as any other suitable industries.

The description of the different illustrative examples has been presented for purposes of illustration and description and is not intended to be exhaustive or limited to the examples in the form disclosed. The different illustrative examples describe components that perform actions or operations. In an illustrative example, a component may be configured to perform the action or operation described. For example, the component may have a configuration or design for a structure that provides the component an ability to perform the action or operation that is described in the illustrative examples as being performed by the component.

Thus, the illustrative examples provide one or more solutions that overcome a problem with detecting moisture in porous structures such as composite sandwich panels. One or more solutions may provide an ability to detect moisture in a porous material including a composite sandwich panel. A controller controls the operation of an electromagnetic radiation system and an infrared detector system to detect a level of moisture using a time window. The selection of the time window can increase the sensitivity of the infrared detector system.

Many modifications and variations will be apparent to those of ordinary skill in the art. Further, different illustrative examples may provide different features as compared to other desirable examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A moisture detection system comprising:
    an electromagnetic radiation system;
    an infrared detector system; and
    a controller in communication with the electromagnetic radiation system and the infrared detector system, wherein the controller is configured to control the electromagnetic radiation system to transmit a pulse of electromagnetic radiation in which the pulse of electromagnetic radiation has multiple wavelengths that are absorbed by water molecules, wherein the multiple wavelengths penetrate a composite sandwich panel at a plurality of depths, and a depth at which moisture is present is determined according to wavelength; and control the infrared detector system to detect an amount of infrared radiation in response to transmitting the pulse of electromagnetic radiation using a time window, wherein the amount of infrared radiation indicates a level of moisture.

2. The moisture detection system of claim 1, wherein the controller is configured to control the electromagnetic radiation system to transmit a pulse of electromagnetic radiation into the composite sandwich panel; and control the infrared detector system to detect an amount of infrared radiation in response to transmitting the pulse of electromagnetic radiation into the composite sandwich panel using the time window selected to detect the amount of infrared radiation when the pulse of electromagnetic radiation heats the composite sandwich panel such that the infrared detector system detects the amount of infrared radiation in the composite sandwich panel when the composite sandwich panel is heated by the pulse of electromagnetic radiation, wherein the amount of infrared radiation indicates the level of moisture in the composite sandwich panel.

3. The moisture detection system of claim 2, wherein the controller is configured to control the infrared detector system to detect an amount of background infrared radiation prior to the electromagnetic radiation system transmitting the pulse of electromagnetic radiation.

4. The moisture detection system of claim 3, wherein the controller is configured to determine the level of moisture in the composite sandwich panel using the amount of infrared radiation detected and energy in the pulse of electromagnetic radiation sent into the composite sandwich panel.

5. The moisture detection system of claim 2, wherein the time window is selected to detect the amount of infrared radiation in response to the pulse of electromagnetic radiation heating the composite sandwich panel such that a sensitivity of the infrared detector system is increased.

6. The moisture detection system of claim 2, wherein the controller is configured to select a number of frequencies for the pulse of electromagnetic radiation based on a desired depth at which the pulse of electromagnetic radiation penetrates the composite sandwich panel.

7. The moisture detection system of claim 2, wherein the controller is configured to generate at least one of a thermal map or a thermal image of infrared radiation for the composite sandwich panel using the amount of infrared radiation detected by the infrared detector system within the time window.

8. The moisture detection system of claim 2, wherein the controller is configured to control the electromagnetic radiation system to transmit the pulse of electromagnetic radiation through a lens antenna to form an electromagnetic radiation beam directed at the composite sandwich panel such that the composite sandwich panel is heated above an ambient temperature for the composite sandwich panel.

9. The moisture detection system of claim 2, wherein the pulse of electromagnetic radiation has a number of frequencies selected from about 300 MHz to about 300 GHz.

10. The moisture detection system of claim 2, wherein the composite sandwich panel comprises a first face sheet, a second face sheet, and a core located between the first face sheet and the second face sheet, wherein the core is selected from at least one of a foam core, an open cell foam core, a closed cell foam core, or a honeycomb core.

11. The moisture detection system of claim 2, wherein the composite sandwich panel is for an aerospace vehicle, which is selected from one of an airplane, an aircraft, a commercial airplane, a rotorcraft, a spacecraft, a commercial spacecraft, and a space plane.

12. A method for detecting moisture in a composite sandwich panel for an aerospace vehicle, the method comprising:
    transmitting a pulse of electromagnetic radiation into the composite sandwich panel such that the composite sandwich panel is heated above an ambient temperature, wherein the pulse of electromagnetic radiation has multiple wavelengths such that the pulse penetrates the composite sandwich panel at a plurality of depths, and a depth at which moisture is present is determined according to wavelength; and
    detecting an amount of infrared radiation generated in the composite sandwich panel in response to transmitting the pulse of electromagnetic radiation into the composite sandwich panel using a time window selected to detect the amount of infrared radiation when the pulse of electromagnetic radiation heats the composite sandwich panel, wherein the amount of infrared radiation detected indicates a level of moisture in the composite sandwich panel.

13. The method of claim 12 further comprising:
    determining the level of moisture in the composite sandwich panel using the amount of infrared radiation detected and energy in the pulse of electromagnetic radiation sent into the composite sandwich panel.

14. The method of claim 12 further comprising:
    selecting the time window to detect the amount of infrared radiation when the pulse of electromagnetic radiation heats the composite sandwich panel above the ambient temperature such that a sensitivity of an infrared detector system is increased.

15. The method of claim 12 further comprising:
    selecting a number of frequencies for the pulse of electromagnetic radiation based on a desired depth at which the pulse of electromagnetic radiation penetrates the composite sandwich panel.

16. The method of claim 12 further comprising:
    generating a thermal image of the amount of infrared radiation for the composite sandwich panel using the amount of infrared radiation detected in the time window.

17. The method of claim 12, further comprising performing an action with respect to the composite sandwich panel, the action comprising
    transmitting additional electromagnetic radiation into the composite sandwich panel such that the level of moisture inside of the composite sandwich panel is reduced.

18. The method of claim 12, further comprising performing an action, wherein the action is selected from one of reworking the composite sandwich panel and replacing the composite sandwich panel.

19. The method of claim 12, wherein transmitting the pulse of electromagnetic radiation into the composite sandwich panel comprises:
   transmitting the pulse of electromagnetic radiation through a lens antenna to form a pulse of electromagnetic radiation beam directed at the composite sandwich panel such that the composite sandwich panel is heated above the ambient temperature for the composite sandwich panel.

20. The method of claim 12, wherein the transmitting and detecting steps are performed while the composite sandwich panel is installed in the aerospace vehicle.

21. The method of claim 12, wherein the transmitting and detecting steps are performed prior to installation of the composite sandwich panel in the aerospace vehicle.

22. The method of claim 12, wherein the pulse of electromagnetic radiation has a number of frequencies selected from about 300 MHz to about 300 GHz.

23. The method of claim 12, wherein the composite sandwich panel comprises a first face sheet, a second face sheet, and a core located between the first face sheet and the second face sheet, wherein the core is selected from at least one of a foam core, an open cell foam core, a closed cell foam core, or a honeycomb core.

24. The method of claim 12, wherein the aerospace vehicle is selected from one of an airplane, an aircraft, a commercial airplane, a rotorcraft, a spacecraft, a commercial spacecraft, and a space plane.

25. A moisture detection system comprising:
   an electromagnetic radiation system;
   an infrared detector system configured to detect an amount of infrared radiation; and
   a controller configured to control the electromagnetic radiation system to transmit a pulse of electromagnetic radiation into a porous material in which a pulse of electromagnetic radiation beam has multiple wavelengths that are absorbed by water molecules such that the pulse penetrates the porous material at a plurality of depths, and a depth at which moisture is present is determined according to wavelength; control the infrared detector system to detect the amount of infrared radiation in the porous material in response to transmitting the pulse of electromagnetic radiation into the porous material using a time window that captures when the pulse of electromagnetic radiation heats the porous material such that the infrared detector system detects the amount of infrared radiation in the porous material when the porous material is heated by the pulse of electromagnetic radiation; and identify a level of moisture in the porous material using an amount of energy in the pulse of electromagnetic radiation transmitted and the amount of infrared radiation detected.

26. The moisture detection system of claim 25, wherein the controller selects a number of frequencies for the pulse of electromagnetic radiation based on a desired depth at which the pulse of electromagnetic radiation penetrates a composite sandwich panel.

27. The moisture detection system of claim 25, wherein the porous material is selected from a group comprising a composite panel, a composite sandwich panel, and a monument for an interior of an aerospace vehicle.

28. A method for detecting moisture in a porous material, the method comprising:
   transmitting electromagnetic radiation into the porous material, wherein an electromagnetic radiation beam has multiple wavelengths that are absorbed by water molecules such that the electromagnetic radiation beam penetrates the porous material at a plurality of depths, and a depth at which moisture is present is determined according to wavelength; and
   detecting an amount of infrared radiation in the porous material in response to transmitting the electromagnetic radiation into a composite sandwich panel using a time window selected to detect the amount of infrared radiation when the electromagnetic radiation heats the porous material; and
   identifying a level of moisture in the porous material using an amount of energy in the electromagnetic radiation transmitted and the amount of infrared radiation detected.

29. The method of claim 28, wherein the porous material is selected from a group comprising a composite panel, the composite sandwich panel, and a monument for an interior of an aerospace vehicle.

30. The method of claim 28 further comprising:
   selecting the time window to detect the amount of infrared radiation when the electromagnetic radiation heats the porous material above an ambient temperature such that a sensitivity of an infrared detector system is increased.

31. The method of claim 28 further comprising:
   selecting a number of frequencies for a pulse of the electromagnetic radiation based on a desired depth at which the electromagnetic radiation penetrates the composite sandwich panel.

* * * * *